(12) United States Patent
Wawrzyniak et al.

(10) Patent No.: US 8,377,507 B2
(45) Date of Patent: Feb. 19, 2013

(54) METHOD AND APPARATUS FOR APPLYING A SEALANT

(75) Inventors: Kortney Wawrzyniak, West Chester, PA (US); Andreas Carl Pfahnl, Eden Prairie, MN (US); John Owen White, Lakeville, MN (US)

(73) Assignee: Synthes USA, LLC, West Chester, PA (US)

( * ) Notice: Subject to any disclaimer, the term of this patent is extended or adjusted under 35 U.S.C. 154(b) by 385 days.

(21) Appl. No.: 12/774,903

(22) Filed: May 6, 2010

(65) Prior Publication Data

US 2010/0310782 A1 Dec. 9, 2010

Related U.S. Application Data

(60) Provisional application No. 61/175,926, filed on May 6, 2009, provisional application No. 61/175,940, filed on May 6, 2009.

(51) Int. Cl.
*A61M 5/00* (2006.01)
*A61M 37/00* (2006.01)
*B05C 5/00* (2006.01)
*B05D 5/10* (2006.01)
*B01F 15/00* (2006.01)

(52) U.S. Cl. ............... 427/207.1; 427/445; 366/139; 366/189; 604/82; 604/191; 118/612

(58) Field of Classification Search .............. 427/207.1, 427/445; 366/139, 189; 604/82, 191; 118/612
See application file for complete search history.

(56) References Cited

U.S. PATENT DOCUMENTS

| | | | |
|---|---|---|---|
| 4,735,616 A | 4/1988 | Eibl et al. | |
| 7,837,656 B2* | 11/2010 | Tarinelli | 604/191 |
| 2006/0227653 A1 | 10/2006 | Keller | |
| 2008/0195040 A1 | 8/2008 | Clark et al. | |
| 2010/0010473 A1* | 1/2010 | D'Alessio et al. | 604/520 |
| 2011/0245866 A1* | 10/2011 | Cassingham et al. | 606/213 |

FOREIGN PATENT DOCUMENTS

| WO | WO 99/32173 | 7/1999 |
|---|---|---|
| WO | WO 2007/008925 | 1/2007 |
| WO | WO 2009/117838 | 10/2009 |

* cited by examiner

*Primary Examiner* — Timothy Vanoy
(74) *Attorney, Agent, or Firm* — Woodcock Washburn LLP

(57) ABSTRACT

A method and apparatus for applying a sealant includes a first chamber that retains a first substance. A second chamber retains a second substance, wherein the second chamber is in selective fluid communication with the first chamber. A third chamber retains a third substance. A first actuator is configured to cause fluid communication of the first and second chambers to allow the first and second substances to comingle and form a first mixture. A second actuator is configured to urge the first mixture and the third substance out of the sealant application apparatus.

35 Claims, 21 Drawing Sheets

Fig. 8

METHOD AND APPARATUS FOR APPLYING A SEALANT

CROSS-REFERENCE TO RELATED APPLICATIONS

This application claims the benefit of U.S. Provisional Patent Application Ser. No. 61/175,926, filed on May 6, 2009 and U.S. Provisional Patent Application Ser. No. 61/175,940, filed May 6, 2009, the disclosures of which are hereby incorporated by reference as if set forth in its entirety herein.

BACKGROUND

Neurosurgery procedures that involve gaining access to the brain typically require removal of a cranial bone flap and an incision made in the underlying dural tissue. After the procedure is completed, the dural tissue is typically sutured to limit cerebrospinal fluid (CSF) leakage. However, post-surgical CSF leakage is possible even with sutures in place. Such CSF leakage is generally undesirable and is generally a condition that is to be avoided.

One way to help avoid post-surgical CSF leakage is to apply a tissue sealant to the area around the incision in the dural tissue. Typically, the tissue sealant is sprayed topically over the suture line. Such tissue sealants act as a mechanical barrier and typically include properties favorable for adherence to tissue, specifically the dural tissue. Examples of sealants include fibrin sealants which can be derived from plasma, for instance, and synthetic sealants.

SUMMARY

It is desired to provide a sealant application apparatus that overcomes shortcomings of conventional applicators.

In accordance with one embodiment, a sealant application apparatus includes a first chamber including a first substance, a second chamber including a second substance, wherein the second chamber is in selective fluid communication with the first chamber, and a third chamber including a third substance. A first actuator is configured to cause fluid communication of the first and second chambers to allow the first and second substances to comingle and form a first mixture. A second actuator configured to urge the first mixture and the third substance out of the sealant application apparatus.

BRIEF DESCRIPTION OF THE DRAWINGS

The foregoing summary, as well as the following detailed description of an example embodiment of the application, will be better understood when read in conjunction with the appended drawings, in which there is shown in the drawings an example embodiment for the purposes of illustration. It should be understood, however, that the application is not limited to the precise arrangements and instrumentalities shown. In the drawings:

FIG. 8 is a cut-away perspective view of a sealant application apparatus constructed in accordance with another alternative embodiment;

DETAILED DESCRIPTION

Figure 1:
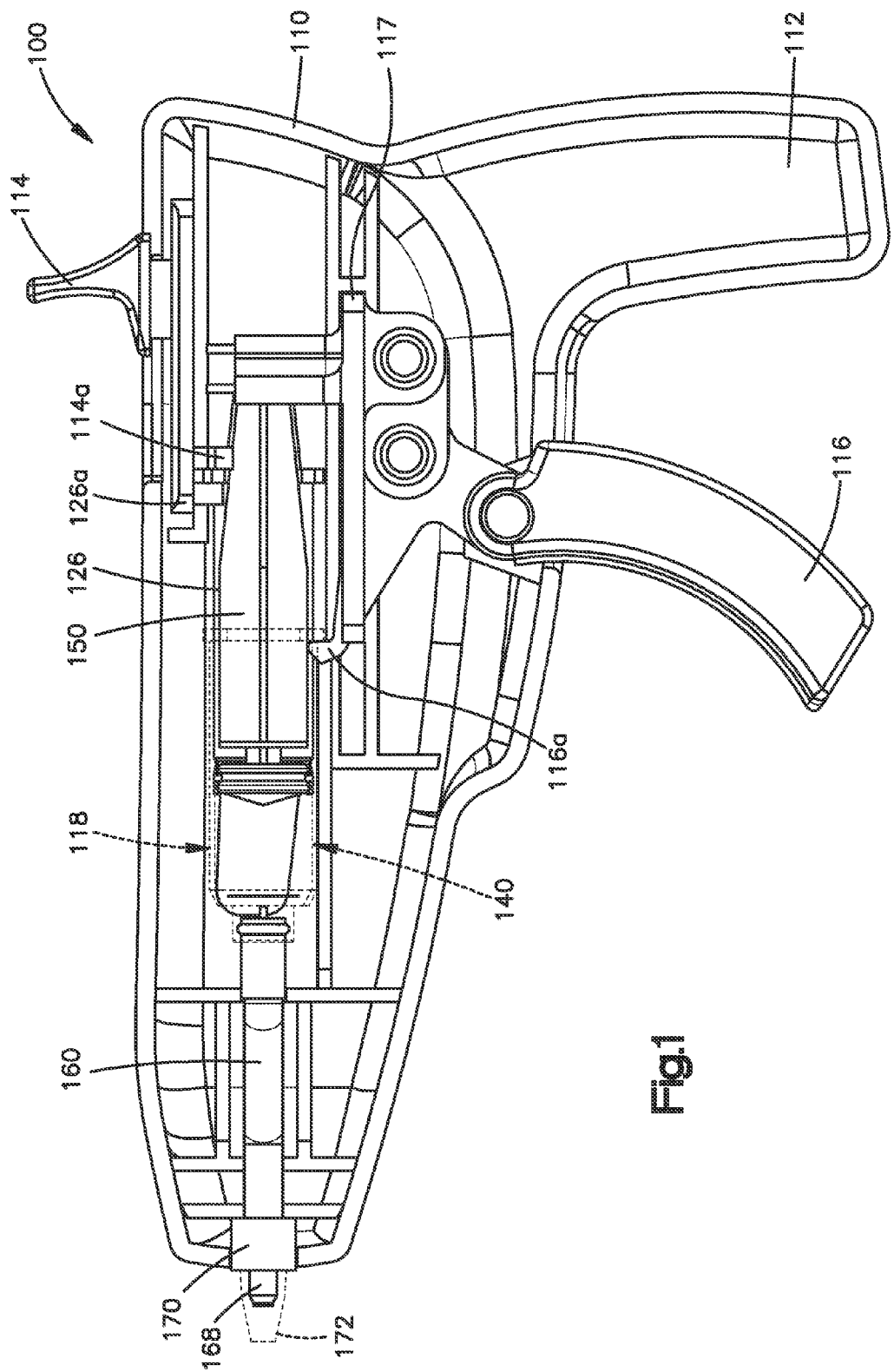
FIG. 1 is a cut-away side elevation view of a sealant application apparatus constructed in accordance with one embodiment.
Figure 2:
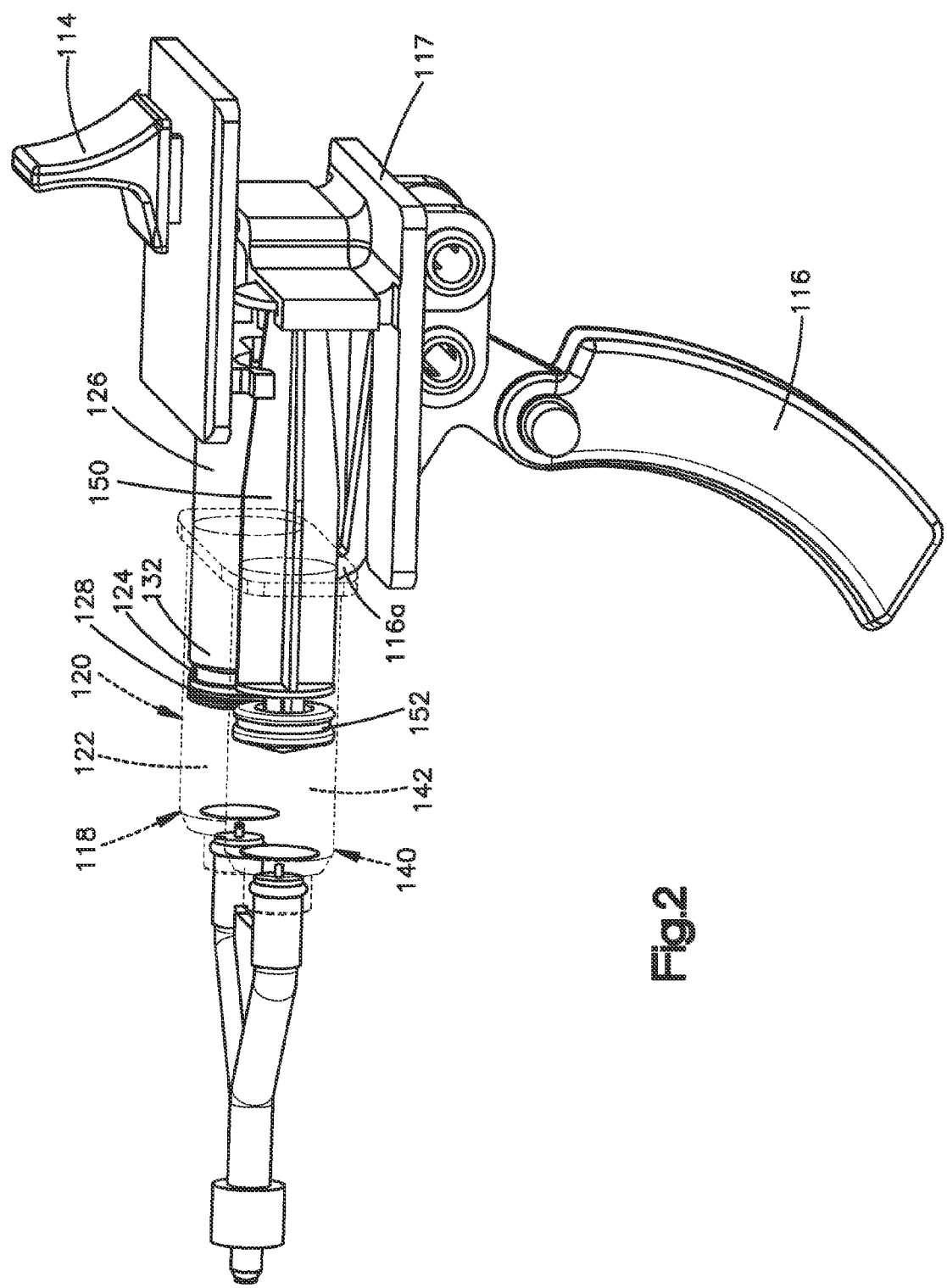
FIG. 2 is a side perspective view of internal components of the sealant application apparatus of FIG. 1.

Referring to FIGS. 1 and 2, in some examples, a sealant application apparatus 100 includes a housing 110 surrounding internal components of the apparatus 100. In an example, the apparatus 100 includes a tissue sealant application apparatus 100. In an example, the housing 110 includes a handle 112 sized and shaped for ergonomically holding and operating the apparatus 100. In a further example, the housing 110 is pistol-shaped. The apparatus 100 can be used to house an amount of components for sealant (a tissue sealant, for instance), which, in some examples, during use of the apparatus 100, are mixed together and expelled from the apparatus 100 at a desired location (a dural tissue incision, for instance) to aid in sealing the location to protect against leakage (CSF leakage from the incision, for instance).

Included with the internal components of the apparatus, in some examples, are chambers for housing components of the sealant. In an example, the apparatus 100 includes a first chamber 122 including, or configured to receive or include, a first substance, a second chamber 124 including, or configured to receive or include, a second substance, and a third chamber 142 including, or configured to receive or include, a third substance. In other examples, the apparatus can include more or fewer that three chambers, depending upon how many substances are to be kept separated prior to usage of the apparatus 100 (for instance, during storage of the apparatus 100). In an example, the apparatus 100 includes lyophilized polyethylene glycol (PEG) in the first chamber 122, reconstitution fluid in the second chamber 124 for reconstituting the lyophilized PEG, and a periodate and water mixture in the third chamber 142. It should be appreciated that the chambers 122, 124, and 142 can initially be provided with the respective substances, or can be provided as empty such that the substances can later be introduced into the chambers as desired.

Referring now to FIGS. 1-5, in an example, the apparatus 100 includes a first syringe 120 and a second syringe 140. The first and second syringes 120, 140 can be joined together in an example using a dual syringe sleeve 118. The dual syringe sleeve, in an example, allows the first and second syringes 120, 140 to move together during use of the apparatus 100, as will be described in more detail below.

In an example, the first syringe 120 includes a first syringe sleeve 118A defining the first chamber 122 at a distal end of the first syringe 120. As stated above, the first substance can be included within the first chamber 122. In an example, the first syringe 120 includes an inner syringe sleeve 126 disposed within the first syringe sleeve 118A proximal from the first chamber 122. The inner syringe sleeve 126, in some examples, can be selectively actuated to telescope within the first syringe sleeve 118A during use of the apparatus 100. The inner syringe sleeve 126, in some examples, can be kept stationary within the first syringe sleeve 118A in some aspects of use of the apparatus 100. In an example, the inner syringe sleeve 126 includes a first plunger 130 telescopically received within the inner syringe sleeve 126. The inner syringe sleeve 126 can include a first plunger tip 132 at a distal end of the first plunger 130. In an example, a second chamber 124 is formed between a distal end of the inner syringe sleeve 126 and the first plunger tip 132. As stated above, a second substance can be disposed within the second chamber 124.

In some examples, a burst disc 128 is disposed at the distal end of the inner syringe sleeve 126, with the burst disc 128 forming at least a substantially sealed distal end of the inner syringe sleeve 126. In an example, the burst disc 128 includes a sealing member around an outer circumferential surface of the burst disc 128 to sealingly engage an inner surface of the first syringe sleeve 118A. In this way, the burst disc 128 can separate the first and second chambers 122, 124, and, in turn, separate the first and second substances (for instance, during storage of the apparatus 100) until a point where it is desired to mix the first and second substances (for instance during use of the apparatus 100). In an example, the burst disc 128 includes a burst disc membrane 129, which can be configured to burst, rupture, or otherwise allow fluid communication therethrough at a certain pressure. Although the burst disc 128 has been described as separating the first and second chambers 122, 124, it is further contemplated that other types of separation members, such as a valve, for instance, are used, provided the other types of separation members are capable of selectively sealingly separating the first and second chambers 122, 124.

The inner syringe sleeve 126, in an example, can be moved telescopically with respect to the first syringe sleeve 118A and the first plunger 130 to selectively create pressure within the second chamber 124 and on the burst disc membrane 129, which, at a certain pressure, will cause the burst disc membrane 129 to rupture, thereby allowing contents (for instance, the first substance) of the first chamber 122 to comingle with contents (for instance, the second substance) of the second chamber 124. Once the burst disc membrane 129 is ruptured, the inner syringe sleeve 126 can then be moved back and forth with respect to the first syringe sleeve 118A and the first plunger 130 to agitate and mix the contents of the first and second chambers 122, 124 (for instance, to reconstitute the lyophilized PEG from the first chamber 122 using the reconstitution fluid from the second chamber 124).

In some examples, the inner syringe sleeve 126 is coupled to a first actuator 114, which is accessible by a user to enable the user to move the inner syringe sleeve 126. In an example, a portion 126A of the inner syringe sleeve 126 is engaged with a portion 114A of the first actuator 114. In the example shown in FIGS. 1-5, a radially extending proximal rim 126A of the inner syringe sleeve 126 is disposed within a channel portion 114A of the first actuator 114 to allow back and forth movement of the first actuator 114 to telescopically move the inner syringe sleeve 126 with respect to the first syringe sleeve 118A and the first plunger 130. In an example, a portion of the first actuator 114 extends outwardly from the housing 110 to allow the user to grip and move the first actuator 114. In an example, the first actuator 114 is slidable with respect to the housing 110.

The second syringe 140, in an example, includes a second plunger 150 slidably received within a second syringe sleeve 118B. The second plunger 150 can include a second plunger tip 152 at a distal end of the second plunger 150. In an example, a third chamber 142 is formed between a distal end of the second syringe sleeve 118B and the second plunger tip 152. As stated above, a third substance can be disposed within the third chamber 142. Although described above as a single chamber syringe, in other examples, the second syringe 140 can also be configured like the two-chambered example of the first syringe 130 described above, for instance, if a substance requiring reconstitution is to be stored therein.

In some examples, the first and second plungers 130, 150 are engaged with a carriage 117 disposed within the housing 110. The carriage 117, in one example, is engaged with each of the first and second plungers 130, 150 and is coupled to a second actuator 116, such that movement (for instance, pivotable movement) of the second actuator 116 causes the carriage 117 to push against the first and second plungers 130, 150 in unison. In the example shown in FIGS. 1-5, the second actuator 116 is in the form of a trigger 116, such that the apparatus 100 can be held by the user with the handle 112 placed in the palm of the hand and the trigger 116 can be actuated and/or held by one or more fingers of that hand. In some examples, the apparatus 100 includes an interlock device, which acts to fix the trigger 116 with respect to the housing 110, to help avoid inadvertent or premature actuation of the apparatus 100. The interlock device can take the form of a button, switch, removable pin, or any such device that could be used to fix the trigger 116 with respect to the housing 110.

In some examples, a Y adapter 160 fluidly couples the first and second syringes 120, 140 with a nozzle 168 to expel the contents from the apparatus 100. The Y adapter 160, in some examples, is engaged at a distal end of the dual syringe sleeve 118. The Y adapter 160, in an example, is Y-shaped and includes a single distal end and two branches at a proximal end with one of the branches sealingly engaged at the distal end of the first syringe sleeve 118A and the other of the branches sealingly engaged at the distal end of the second syringe sleeve 118B. In the example shown in FIG. 4, the Y adapter 160 includes seals 166 such as O-ring seals 166 (FIG. 4) at the proximal ends of the Y adapter 160, which sealingly engage with the distal ends of the first and second syringe sleeves 118A, 118B.

In some examples, the nozzle 168 is disposed at the distal end of the Y adapter 160. Fluid passageways can extend from the proximal end of the Y adapter 160, through each of the branches of the Y adapter 160, to the nozzle 168. The nozzle 168, in an example, is a dual nozzle, such that the passageways running from each of the first and second syringes 120, 140 do not converge into a single passageway before or proximal to the nozzle 168. In a further example, a mixing chamber 172 (shown in phantom in FIG. 1) is attached to the distal end of the Y adapter 160, the mixing chamber 172 being configured to allow the contents of the first and second syringes 120, 140 to comingle and mix to form a sealant mixture, for instance. The distal end of the Y adapter 160 can include a collar 170 or other engagement device for attachment of the mixing chamber 172. In an example, the collar 170 is a luer lock collar for engagement of a mixing chamber 172 having a mating luer connection. In another example, the passageways can converge prior to the distal end of the Y-adapter to enable the components to mix prior to leaving the Y adapter, thereby eliminating the need for a separate mixing chamber 172, as described above.

The mixing chamber 172 can include a nozzle to expel the sealant mixture (for example, the tissue sealant) for application to a desired surface (for instance, the dural tissue). In an example, the nozzle is an atomizing nozzle to atomize the sealant mixture during use of the apparatus 100 and facilitate application of the sealant mixture (for example, the tissue sealant) for application to the desired surface (for instance, the dural tissue).

Figure 3:
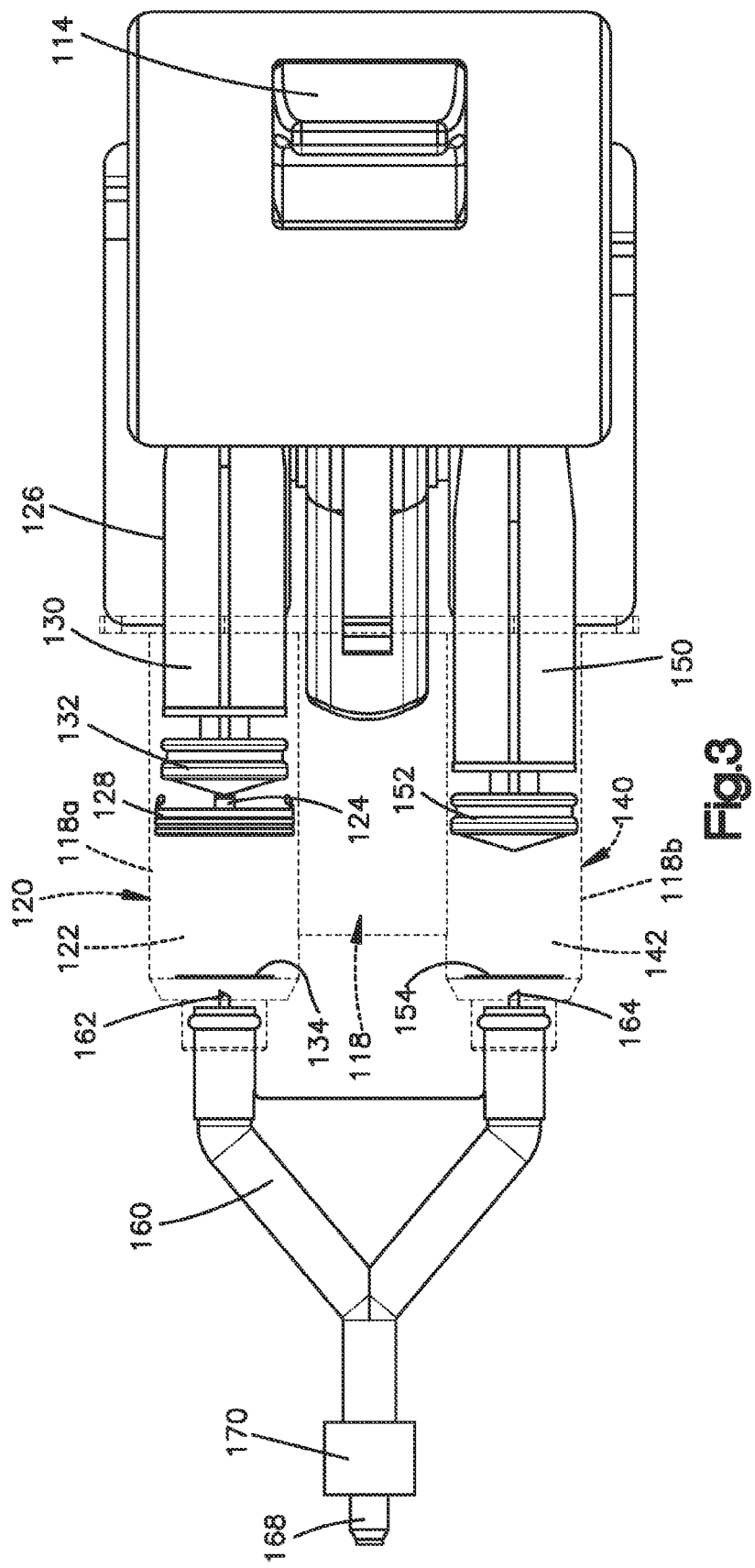
FIG. 3 is a top plan view of internal components of the sealant application apparatus of FIG. 1.
Figure 4:
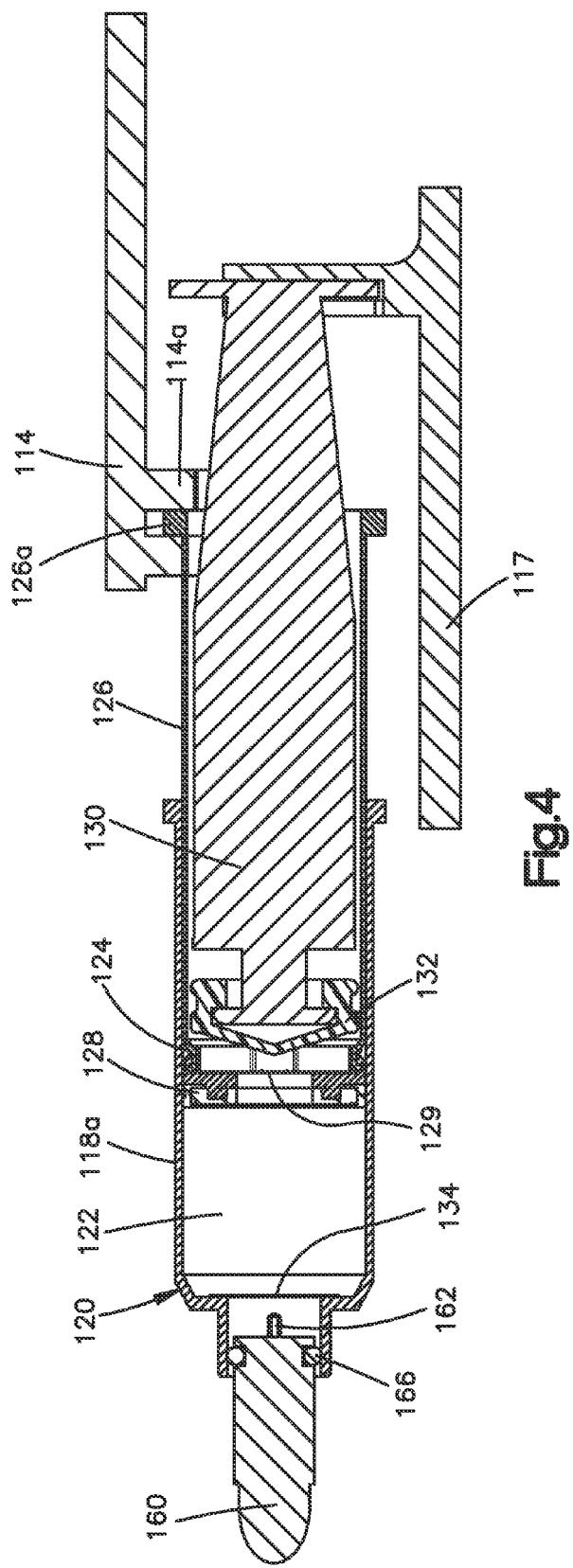
FIG. 4 is a sectional side elevation view of internal components of the sealant application apparatus of FIG. 1.
Figure 5:
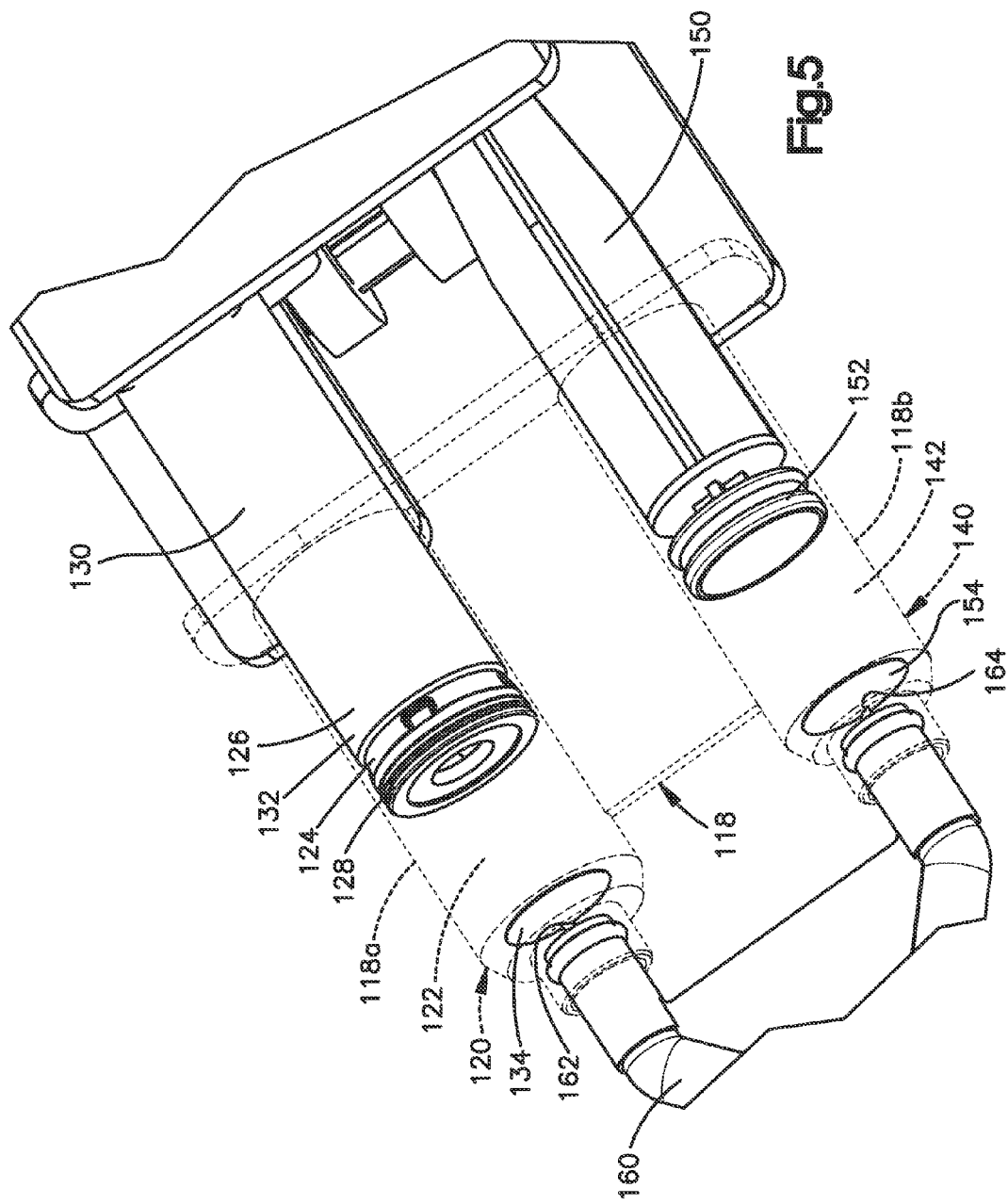
FIG. 5 is a perspective view of internal components of the sealant application apparatus of FIG. 1.

With reference to FIGS. 3 and 4, in some examples, the first and second syringes 120, 140 include first and second puncture seals 134, 154, respectively, to inhibit contamination and leakage of the contents of the first and second syringes 120, 140. In an example, the branches of the Y adapter 160 include proximally extending first and second puncture members 162, 164. In an example, the first and second puncture members 162, 164 can be used to puncture the first and second puncture seals 134, 154 to allow the contents of the first and second syringes 120, 140 to be urged from the first and second syringes 120, 140 and into the Y adapter 160. For instance, the first and second puncture seals 134, 154 can be punctured when it is desired to apply sealant mixture using the apparatus 100. In some examples, the first and second puncture seals 134, 154 are moved relative to the first and second puncture members 162, 164 in order to bring the first and second puncture members 162, 164 into contact with and puncture the first and second puncture seals 134, 154. In the example shown in FIGS. 3 and 4, the dual syringe sleeve 118 can be moved distally with respect to the Y adapter 160 to allow the first and second puncture members 162, 164 to pierce the first and second puncture seals 134, 154 and allow fluid communication of the first and second syringes 120, 140 and the Y adapter 160. In this example, the O-ring seals 166 can maintain the seal between the Y adapter 160 and the distal ends of the first and second syringe sleeves 118A, 118B during movement of the dual syringe sleeve 118. In an example, the trigger 116 includes a hook 116A which engages the dual syringe sleeve 118 and inhibits movement of the dual syringe sleeve 118 and lessens the likelihood of premature or unintended piercing of the first and second puncture seals 134, 154. In a further example, actuation of the trigger 116 initially removes the hook 116A from engagement with the dual syringe sleeve 118 and subsequently moves the dual syringe sleeve 118 distally so that the first and second puncture members 162, 164 contact and pierce the first and second puncture seals 134, 154.

Referring to the example apparatus 100 shown in FIGS. 1-5 and described above, in use, the user holds the apparatus 100 by the handle 112 using one hand and pulls the first actuator 114 back (proximally with respect to the apparatus 100). Movement of the first actuator 114 causes proximal movement of the inner syringe sleeve 126 with respect to the first syringe sleeve 118A and the first plunger 130 (which is held in place by the carriage 117). This motion of the inner syringe sleeve 126 and the burst disc 128 increase pressure within the second chamber 124, which, when the pressure reaches a certain level, causes the burst disc membrane 129 to rupture, allowing the first and second substances (for instance, the lyophilized PEG and the reconstitution fluid) of the first and second chambers 122, 124 to mix. The first actuator 114 can then be moved back and forth to move the inner syringe sleeve 126 and burst disc 128 back and forth with respect to the first syringe sleeve 118A and the first plunger 130 for a period of time sufficient to agitate and mix the first and second substances. In an example, the housing 110 can include a window to allow the user to view the mixture of the first and second substances to determine whether sufficient mixing of the first and second substances has occurred. Once the first and second substances are sufficiently mixed, the user disengages the interlock mechanism to allow the trigger 116 to be pulled. Initial pulling of the trigger 116 disengages the hook 116A from the dual syringe sleeve 118 and starts motion of the carriage 117 within the housing 110 to push on the first and second plungers 130, 150. Movement of the trigger 116 and carriage 117 initially moves the dual syringe sleeve 118 distally with respect to the housing 110 to cause the first and second puncture members 162, 164 to come into contact with and pierce the first and second puncture seals 134, 154 at the distal ends of the first and second syringe sleeves 118A, 118B. After the first and second puncture seals 134, 154 are pierced, further actuation of the trigger 116 causes the carriage 117 to push the first and second plungers 130, 150 distally with respect to the first and second syringe sleeves 118A, 118B to force the contents of the first and second syringes 120, 140 (for instance, the reconstituted PEG from the first syringe 120 and the periodate and water mixture from the second syringe 140) out of the first and second syringes 120, 140 and into the passageways of the Y adapter 160. In an example, the first plunger tip 132 is moved distally and into contact with the burst disc 128, at which point the first plunger 130, the first plunger tip 132, the burst disc 128, and the inner syringe sleeve 126 are moved in unison (and essentially act together as a syringe plunger) within the first syringe sleeve 118A to force the contents of the first syringe 120 into the Y adapter 160. The contents of the first and second syringes 120, 140 exit the Y adapter 160 through the dual nozzle 168 and enter the mixing chamber 172 to mix together and form the sealant mixture. The sealant mixture is then expelled from the apparatus 100 through the atomizing nozzle of the mixing chamber 172 for application to the desired surface (for instance, the dural tissue incision).

Figure 6:
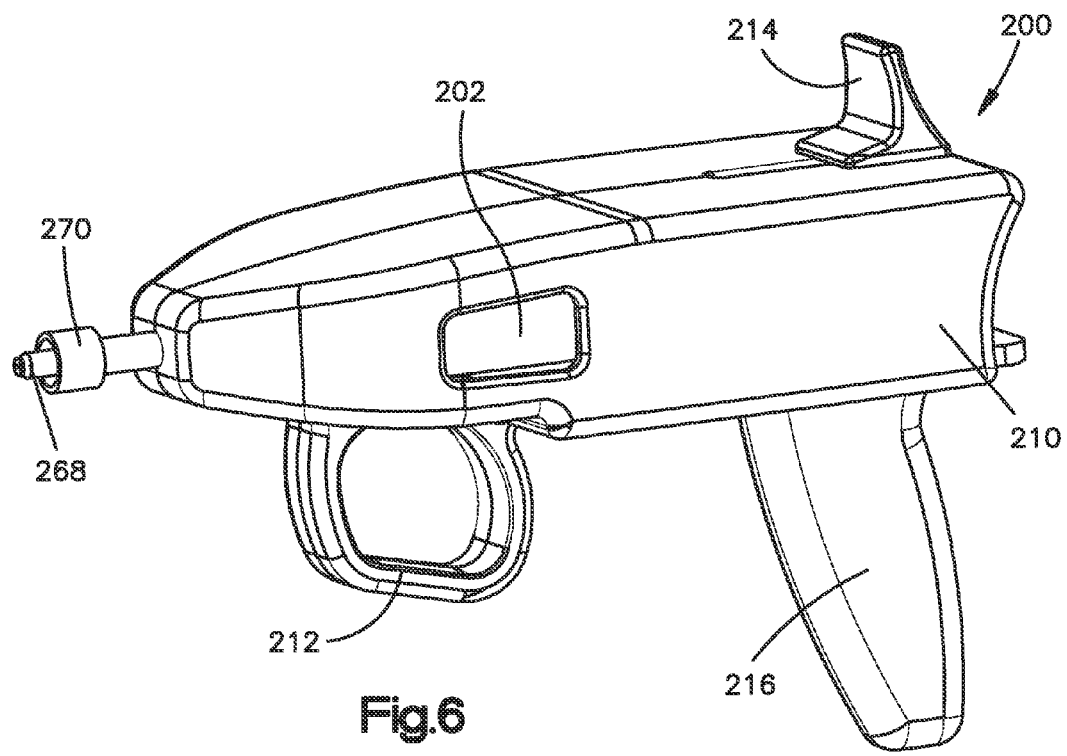
FIG. 6 is a perspective view of a sealant application apparatus constructed in accordance with an alternative embodiment.
Figure 7:
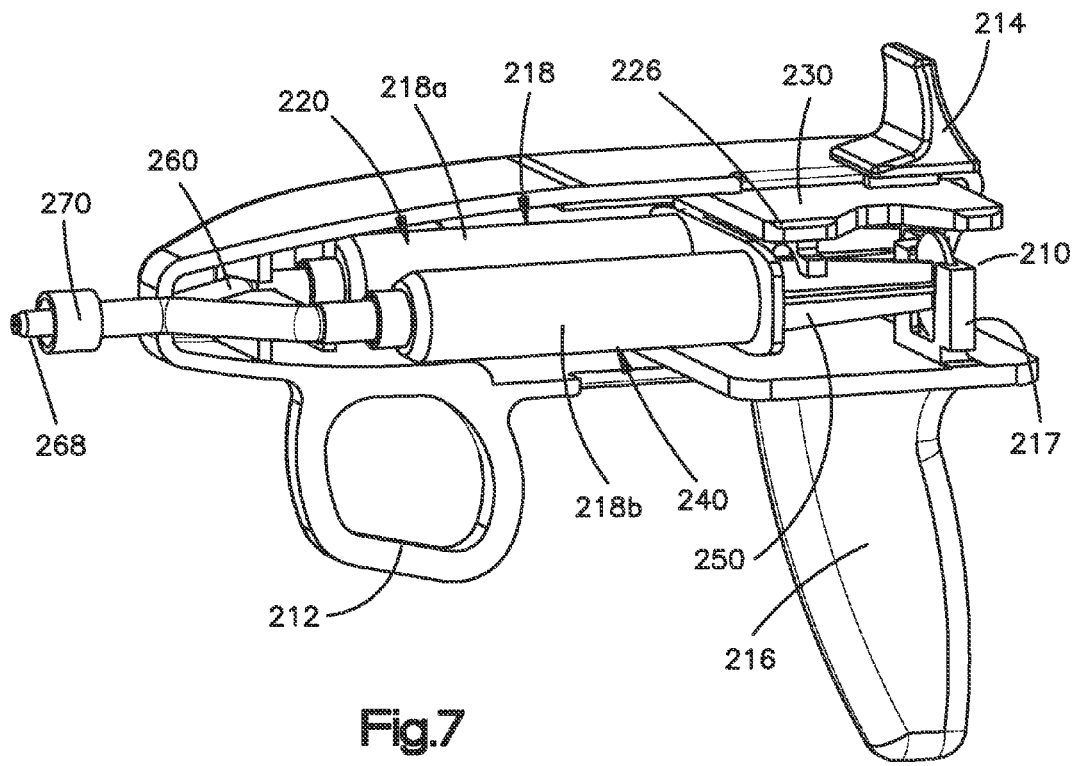
FIG. 7 is a cut-away perspective view of the sealant application apparatus of FIG. 6.

Referring now to FIGS. 6 and 7, in another example, a sealant application apparatus 200 is shown for housing an amount of components for a sealant (a tissue sealant, for instance), which, in some examples, during use of the apparatus 200, are mixed together and expelled from the apparatus 200 at a desired location (a dural tissue incision, for instance) to aid in sealing the location to protect against leakage (CSF leakage from the incision, for instance). In some examples, some aspects of the apparatus 200 are substantially similar to aspects of the apparatus 100 described above. As such, some structures, features, and components of the apparatus 200 are shown in FIGS. 6 and 7 with numbering similar to substantially similar structures, features, and components of the apparatus 100, as shown in FIGS. 1-5, and function in manners substantially similar to those described above with respect to the apparatus 100. Accordingly, the description of such substantially similar features is omitted below and, instead, is incorporated from the corresponding descriptions above with respect to the apparatus 100.

In the example shown in FIGS. 6 and 7, the apparatus 200 includes a housing 210 including a grip or finger loop 212 that is fixed with respect to the housing 210. In an example, the apparatus 200 includes a second actuator 216 that is slidably engaged with respect to the housing 210. In the example of FIGS. 6 and 7, the second actuator 216 is a grip 216 extending from the housing 210 to hold in the palm of a hand of the user with one or more fingers of the user extending through the finger loop 212. With such a configuration, the user can squeeze the hand to pull the finger loop 212 (and the housing 210) toward the grip 216 to actuate the apparatus 200. In some examples, a carriage 217 extends upwardly from a top surface of the grip 216, with the carriage 217 abutting first and second plungers 230, 250 to hold stationary (with respect to the grip 216) the first and second plungers 130, 150 during actuation of the apparatus 200. In an example, a Y adapter 260 is fixed with respect to the housing 210, so as to move rearwardly (along with the housing 210) with respect to the grip 216. In an example, proximal ends of the Y adapter 260 include puncture members substantially similar to those described above with respect to the apparatus 100 to selectively pierce puncture seals of first and second syringes sleeves 218A, 218B of first and second syringes 220, 240. In this way, during initial actuation of the apparatus 200, the Y adapter 260 is moved rearwardly with respect to the first and second syringes sleeves 218A, 218B of a dual syringe sleeve 218 to pierce the puncture seals. After the puncture seals are pierced, the proximal ends of the Y adapter 260 abut the dual syringe sleeve 218, such that continued actuation of the apparatus 200 causes movement of the housing 210, the Y adapter 260, and the dual syringe sleeve 218 with respect to the grip 216 and the first and second plungers 230, 250. In this way, the relative motion of the dual syringe sleeve 218 with respect to the first and second plungers 230, 250 forces the contents of the first and second syringes 220, 240 into the Y adapter 260 and ultimately out of the apparatus 200. In an example, the housing 210 includes windows 202 on one or both sides of the apparatus 200 to enable the user to view the contents of the first and second syringes 220, 240, for instance, to determine whether sufficient mixing of the contents of the first and/or second syringes 220, 240 has occurred.

Referring to the example apparatus 200 shown in FIGS. 6 and 7 and described above, in use, the user holds the apparatus 200 by the grip 216 using one hand and pulls the finger grip 212 toward the grip 216. Movement of a first actuator 214 causes proximal movement of an inner syringe sleeve with respect to the first syringe sleeve 218A and the first plunger 230 (which is held in place by the carriage 217). This motion of the inner syringe sleeve and a burst disc increase pressure within a second chamber, which, when the pressure reaches a certain level, causes a burst disc membrane to rupture, allowing first and second substances (for instance, the lyophilized PEG and the reconstitution fluid) of first and second chambers to mix. The first actuator 214 can then be moved back and forth to move the inner syringe sleeve and burst disc back and forth with respect to the first syringe sleeve 218A and the first plunger 230 for a period of time sufficient to agitate and mix the first and second substances. In an example, the housing 212 can include a window 202 on the side of the first syringe 220 to allow the user to view the mixture of the first and second substances within the first syringe to determine whether sufficient mixing of the first and second substances has occurred. Once the first and second substances are sufficiently mixed, the user disengages an interlock mechanism to allow the finger loop 212 to be pulled toward the grip 216.

Initial pulling of the finger loop 212 moves the housing 210 and the Y adapter back toward the dual syringe sleeve 218 to cause the puncture members to come into contact with and pierce the puncture seals at the distal ends of the first and second syringe sleeves 218A, 218B. After the puncture seals are pierced, further pulling of the finger loop 212 causes the dual syringe sleeve 218 to move rearwardly with the Y adapter 260 and the housing 210. Because the carriage 217 keeps the first and second plungers 230, 250 stationary with respect to the grip 216, the first and second syringe sleeves 218A, 218B are moved over the first and second plungers 230, 250 to force the contents of the first and second syringes 220, 240 (for instance, the reconstituted PEG from the first syringe 220 and a periodate and water mixture from the second syringe 240) out of the first and second syringes 220, 240 and into passages of the Y adapter 260. The contents of the first and second syringes 220, 240 exit the Y adapter 260 through a dual nozzle and enter a mixing chamber to mix together and form the sealant mixture. The sealant mixture is then expelled from the apparatus 200 through an atomizing nozzle of the mixing chamber for application to the desired surface (for instance, the dural tissue incision).

Referring now to FIGS. 8-12, in another example, a sealant application apparatus 300 (for instance, a tissue sealant application apparatus 300) is shown for housing an amount of components for a sealant (a tissue sealant, for instance), which, in some examples, during use of the apparatus 300, are mixed together and expelled from the apparatus 300 at a desired location (a dural tissue incision, for instance) to aid in sealing the location to protect against leakage (CSF leakage from the incision, for instance). In some examples, the apparatus 300 includes a housing 310 surrounding internal components of the apparatus 300. In an example, the housing 310 includes a handle 312 sized and shaped for ergonomically holding and operating the apparatus 300. In a further example, the housing 310 is pistol-shaped.

Included with the internal components of the apparatus, in some examples, are chambers for housing components of the sealant. In an example, the apparatus 300 includes a first chamber 322 including a first substance, a second chamber 342 including a second substance, and a third chamber 324 including a third substance. In other examples, the apparatus can include more or fewer that three chambers, depending upon how many substances are to be kept separated prior to usage of the apparatus 300 (for instance, during storage of the apparatus 300). In an example, the apparatus 300 includes reconstitution fluid in the first chamber 322, a periodate and water mixture in the second chamber 342, and lyophilized PEG in the third chamber 324.

Figure 8:
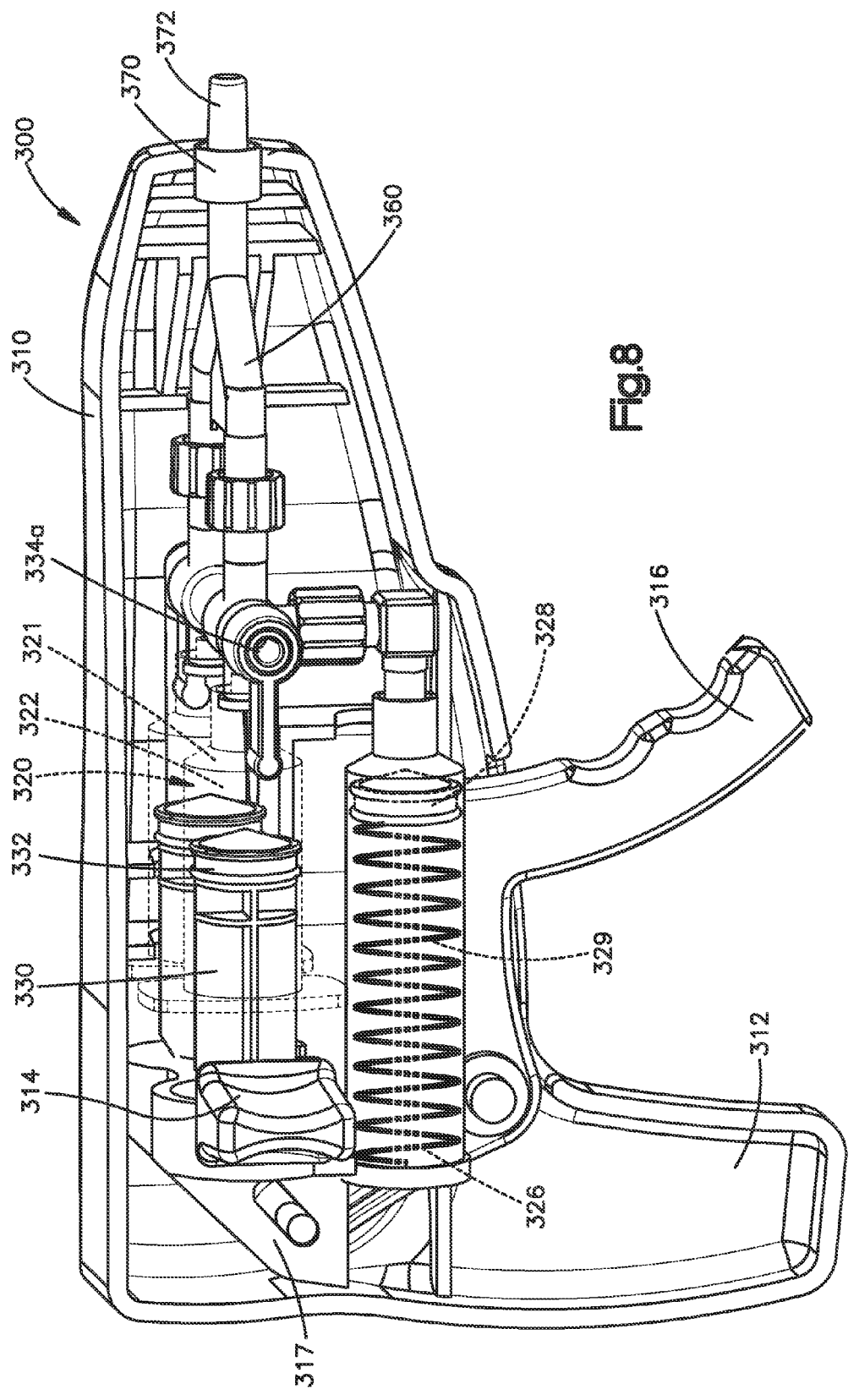
Figure 9:
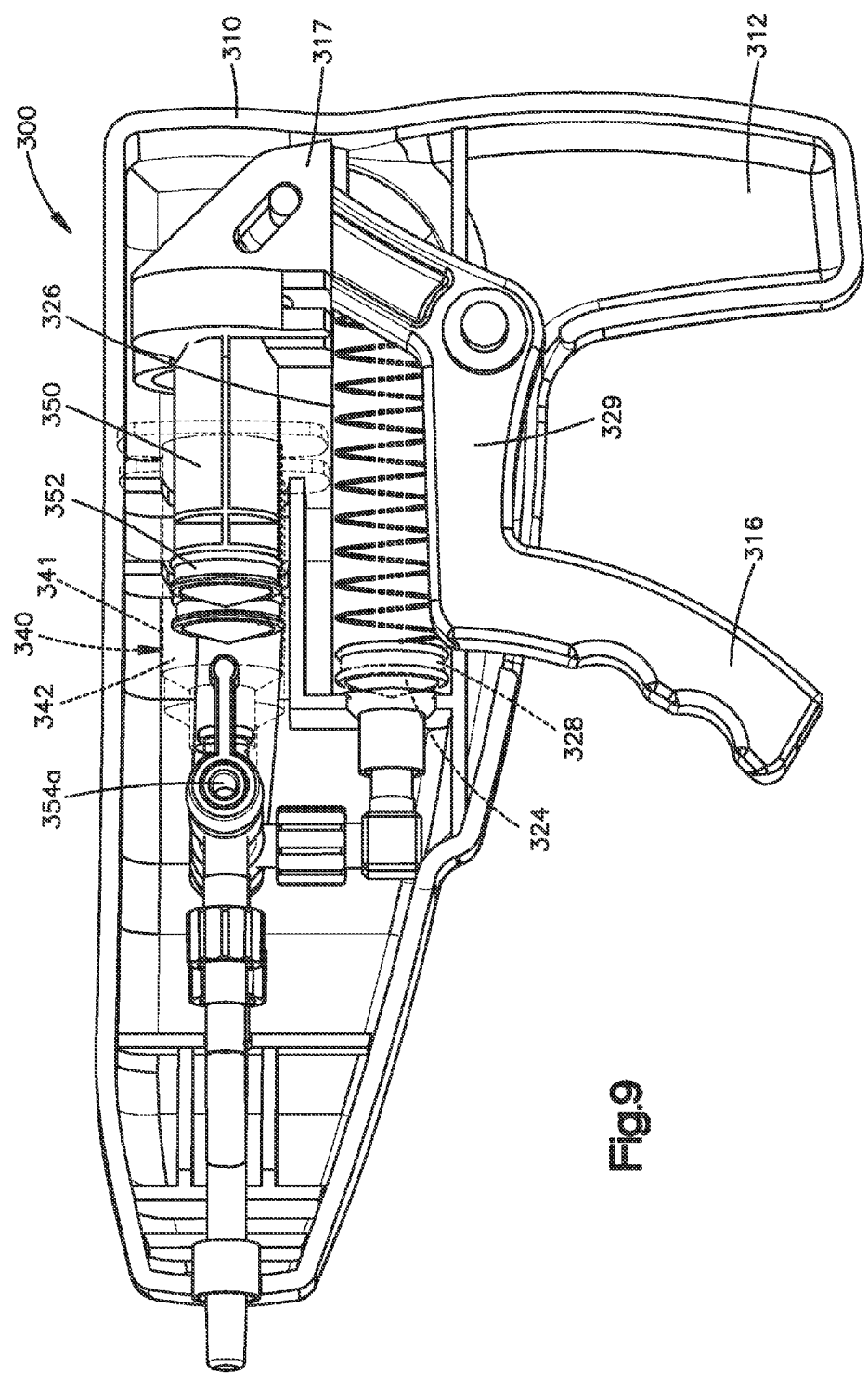
FIG. 9 is a cut-away perspective view of the sealant application apparatus of FIG. 8.

Referring now to FIGS. 8 and 9, in an example, the apparatus 300 includes a first syringe 320 and a second syringe 340. In an example, the first syringe 320 includes a first syringe sleeve 321 having a first syringe plunger 330 slidably disposed within the first syringe sleeve 321. The first syringe plunger 330 can include a first plunger tip 332 disposed at a distal tip of the first syringe plunger 330. In an example, the first chamber 322 is defined between the first plunger tip 332 and a distal end of the first syringe sleeve 321. As stated above, the first substance can be included within the first chamber 322. In an example, the second syringe 340 includes a second syringe sleeve 341 having a second syringe plunger 350 slidably disposed within the second syringe sleeve 341. The second syringe plunger 350 can include a second plunger tip 352 disposed at a distal tip of the second syringe plunger 350. In an example, the second chamber 342 is defined between the second plunger tip 352 and a distal end of the second syringe sleeve 341. As stated above, the second substance can be included within the second chamber 342.

In an example, a third syringe sleeve 326 is disposed within the housing 310. The third syringe sleeve 326, in some examples, includes a third plunger tip 328. In further examples, the third plunger tip 328 is biased toward the distal end of the third syringe sleeve 326. In a still further examples, the third syringe sleeve 326 includes a spring 329 (a compression spring, in one example) disposed between a proximal end of the third syringe sleeve 326 and the third plunger tip 328 to bias the third plunger tip 328 toward the distal end of the third syringe sleeve 326. In an example, the third chamber 324 is defined between the third plunger tip 328 and the distal end of the third syringe sleeve 326. As stated above, the third substance can be included within the third chamber 324.

Figure 10:
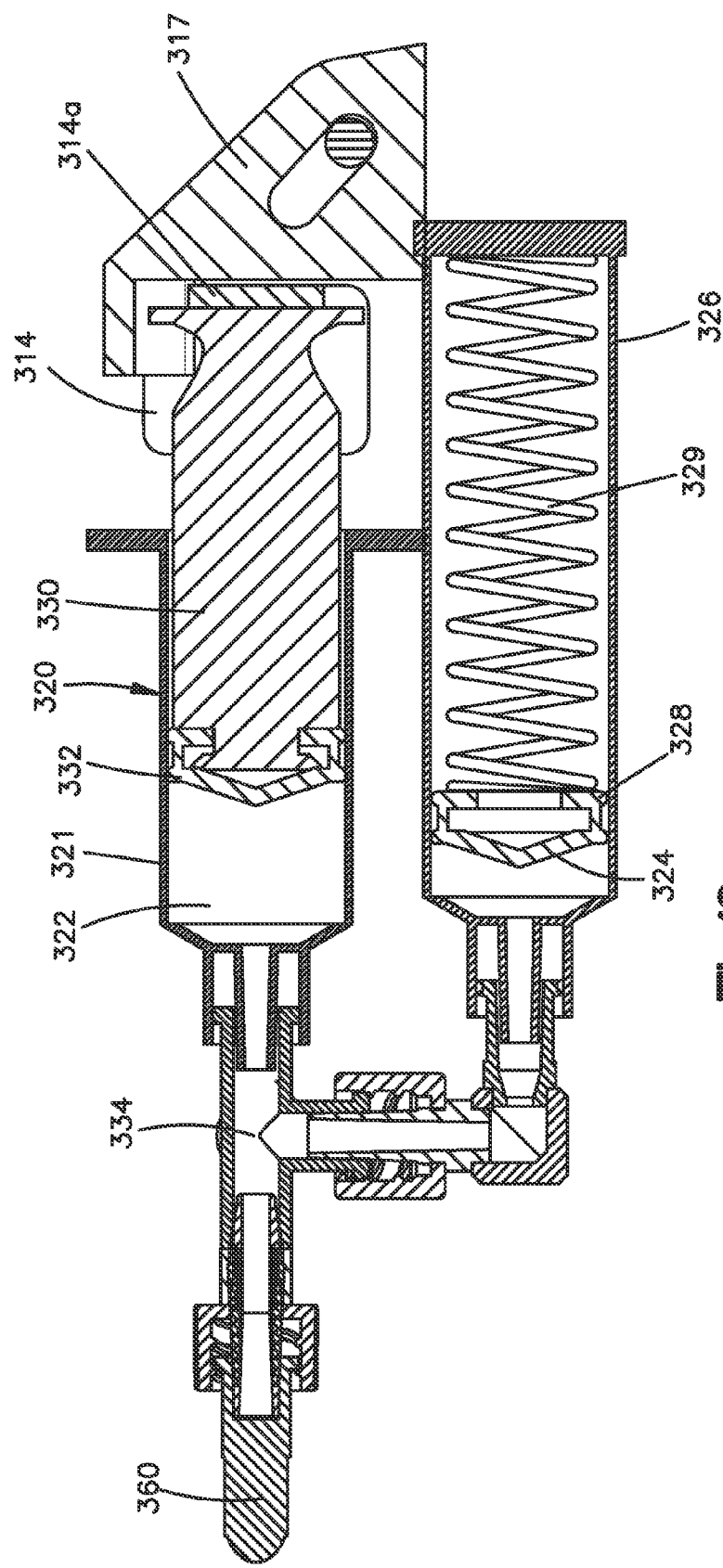
FIG. 10 is a cut-away sectional side elevation view of internal components of the sealant application apparatus of FIG. 8.
Figure 11:
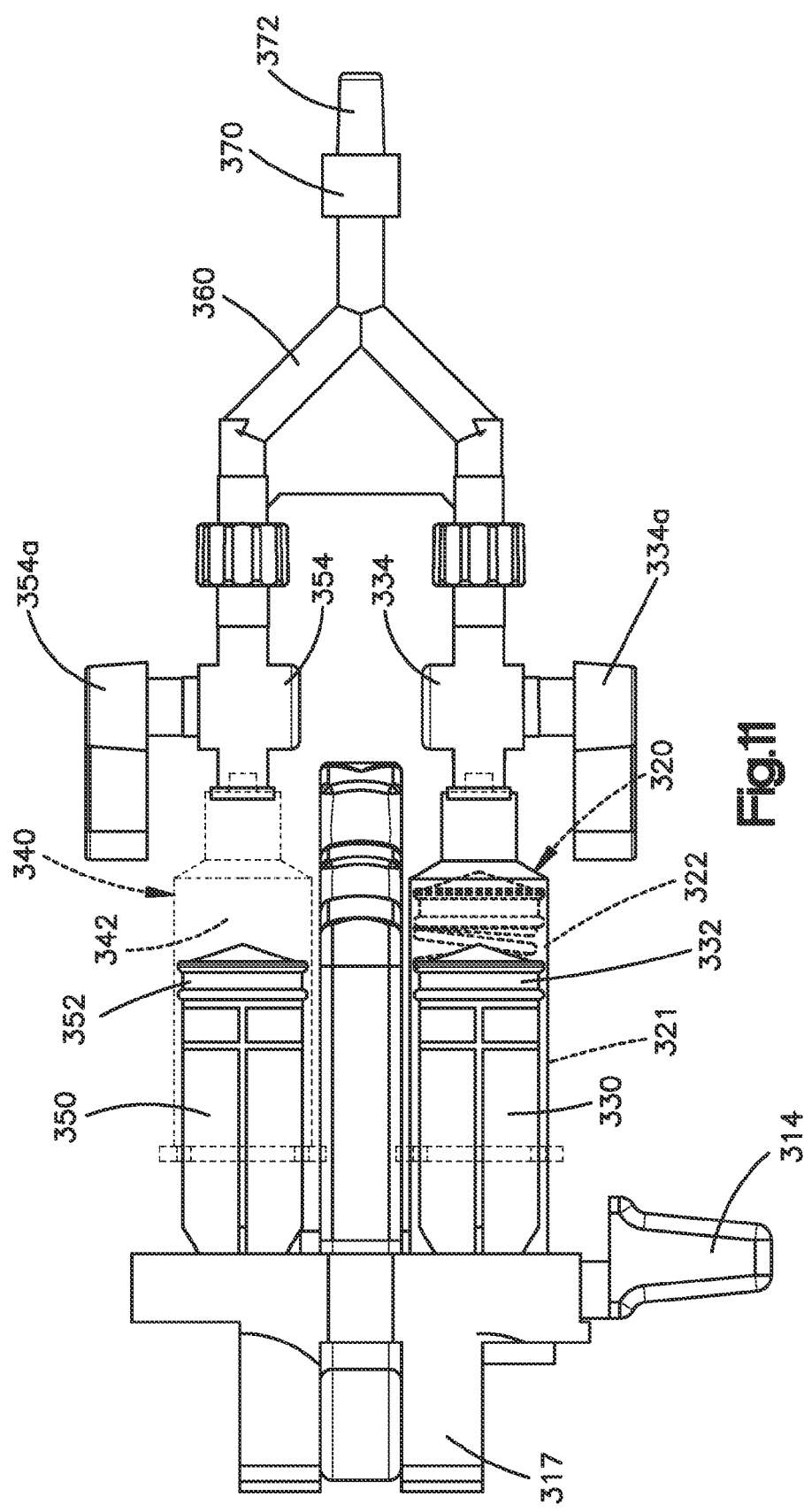
FIG. 11 is a top plan view of internal components of the sealant application apparatus of FIG. 8.

Referring to FIGS. 8, 10, and 11, in some examples, the first and third chambers 322, 324 are selectively fluidly coupled. In an example, a first valve 334 selectively fluidly couples the first and third chambers 322, 324. That is, when a first valve lever 334A is turned to a first position, a passage between the first and third chambers 322, 324 is opened, to allow the first substance to comingle with the third substance. In some examples, the first syringe plunger 330 is coupled to a first actuator 314, which is accessible by the user to enable the user to move the first syringe plunger 330. In an example, a proximal end of the first syringe plunger 330 is engaged with a portion 314A of the first actuator 314, such that back and forth movement of the first actuator 314 causes the first syringe plunger 330 to telescopically move back and forth within the first syringe sleeve 321. Such forward movement of the first actuator 314 causes the first substance to move from the first syringe 320, through the passage, and into the third syringe sleeve 326 to at least partially mix with the third substance. Rearward movement of the first actuator 314 causes suction to force the at least partially mixed first and third substances to pass from the third syringe sleeve 326, through the passage, and into the first syringe 320. In some examples, repeated back and forth motion of the first actuator 314 causes agitation and mixing of the first and third substances. In an example, a portion of the first actuator 314 extends outwardly from the housing 310 to allow the user to grip and move the first actuator 314. In an example, the first actuator 314 is slidable with respect to the housing 310.

In some examples, the spring 329 within the third syringe sleeve 326 moves the third plunger tip 328 distally within the third syringe sleeve as the third substance mixes with the first substance and exits the third chamber 324. For instance, in an example, during mixing of the first substance from the first chamber 322 with the third substance in the third chamber 324, the third plunger 328 moves distally to fill the space in the third chamber 324 previously filled by the third substance. In this way, during mixing of the first and third substances, the spring-biased third plunger 328 forces the first and third substances out of the third syringe sleeve 326 and into the first syringe 320, so that the mixed first and third substances (for instance, the reconstituted PEG) are disposed within the first syringe 320.

The second syringe 340, in an example, also includes a passageway leading from the distal end of the second syringe 340 having a second valve 354 for selectively opening or closing the passageway from the second syringe 340. In an example, the second valve 354 includes a second lever 354A for selectively configuring the second valve 354 to selectively open or close the passageway from the second syringe 340. In a further example, the first and second valves 334, 354 are slaved together such that the user need only actuate one lever to control both valves 334, 354, rather than requiring the user to individually actuate the first and second levers 334A, 354A to control the first and second valves 334, 354. In an example, the second syringe 340 includes the third substance which is a premixed mixture, such as a periodate and water mixture. However, in another example, if it is desirable to mix the third substance with a fourth substance, for instance, the apparatus 300 can include another, fourth syringe fluidly coupled to the second syringe 340 in a manner similar to that described above with respect to the first syringe 320 and third syringe sleeve 326. For instance, a fourth syringe could be used if the second substance were a substance requiring reconstitution.

Referring to FIGS. 8-10, in some examples, the first and second plungers 330, 350 are engaged with a carriage 317 disposed within the housing 310. The carriage 317, in one example, is engaged with each of the first and second plungers 330, 350 and is coupled to a second actuator 316, such that movement (for instance, pivotable movement) of the second actuator 316 causes the carriage 317 to push against the first and second plungers 330, 350 in unison. In an example, the second actuator 316 is in the form of a trigger 316, such that the apparatus 300 can be held by the user with the handle 312 placed in the palm of the hand and the trigger 316 can be actuated and/or held by one or more fingers of that hand. In some examples, the apparatus 300 includes an interlock device, which acts to fix the trigger 316 with respect to the housing 310, to help avoid inadvertent or premature actuation of the apparatus 300. The interlock device can take the form of a button, switch, removable pin, or any such device that could be used to fix the trigger 316 with respect to the housing 310. In some examples, the first and second valves 334, 354 act instead of or in addition to any such interlock device. That is, the first and second valves 334, 354 must be positioned in an open position to allow the contents of the first and second syringes 320, 340 to be forced from the first and second syringes 320, 340 with actuation of the trigger 316.

Figure 12:
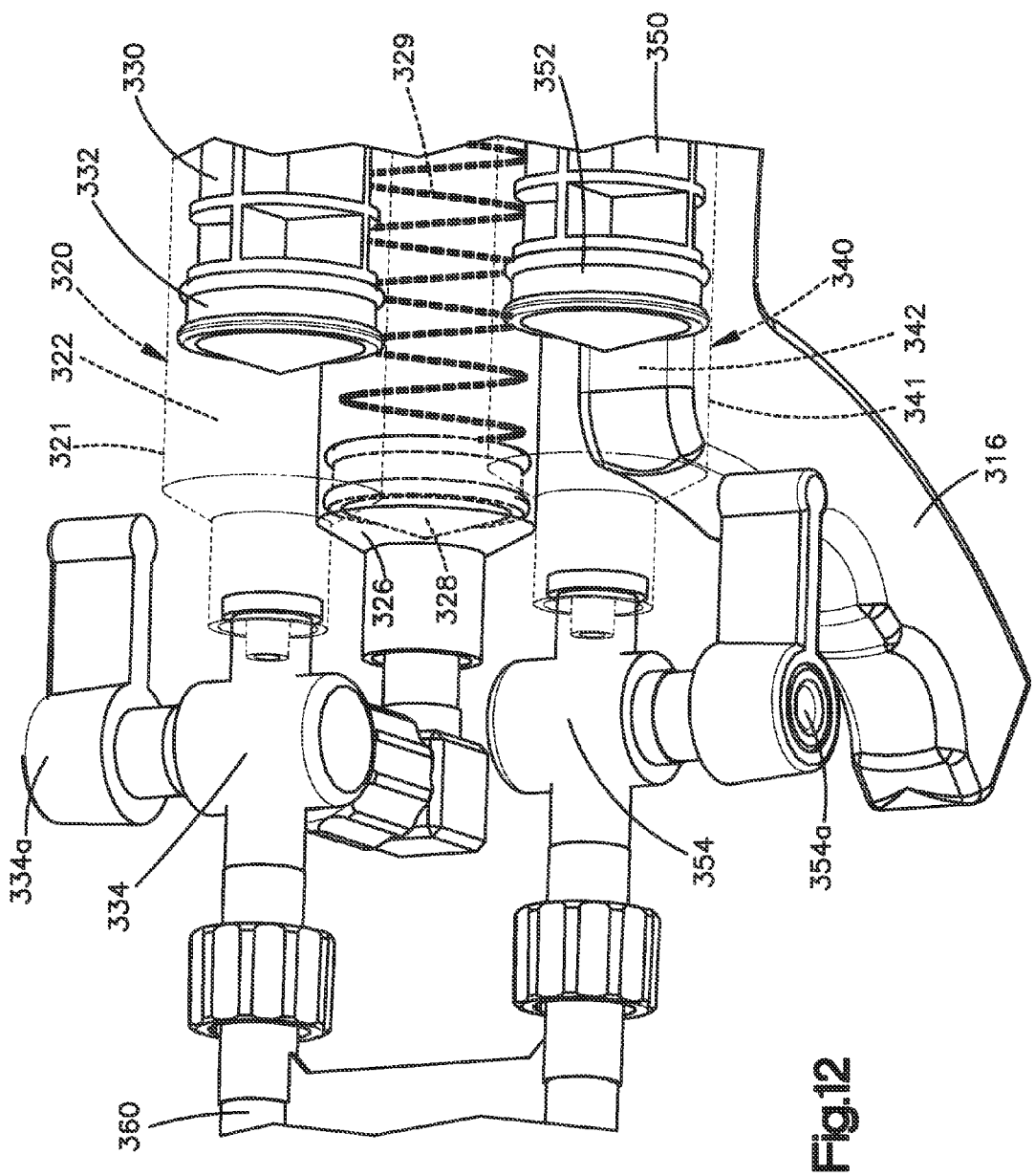
FIG. 12 is an enlarged perspective view of internal components of the sealant application apparatus of FIG. 8.
Figure 13:
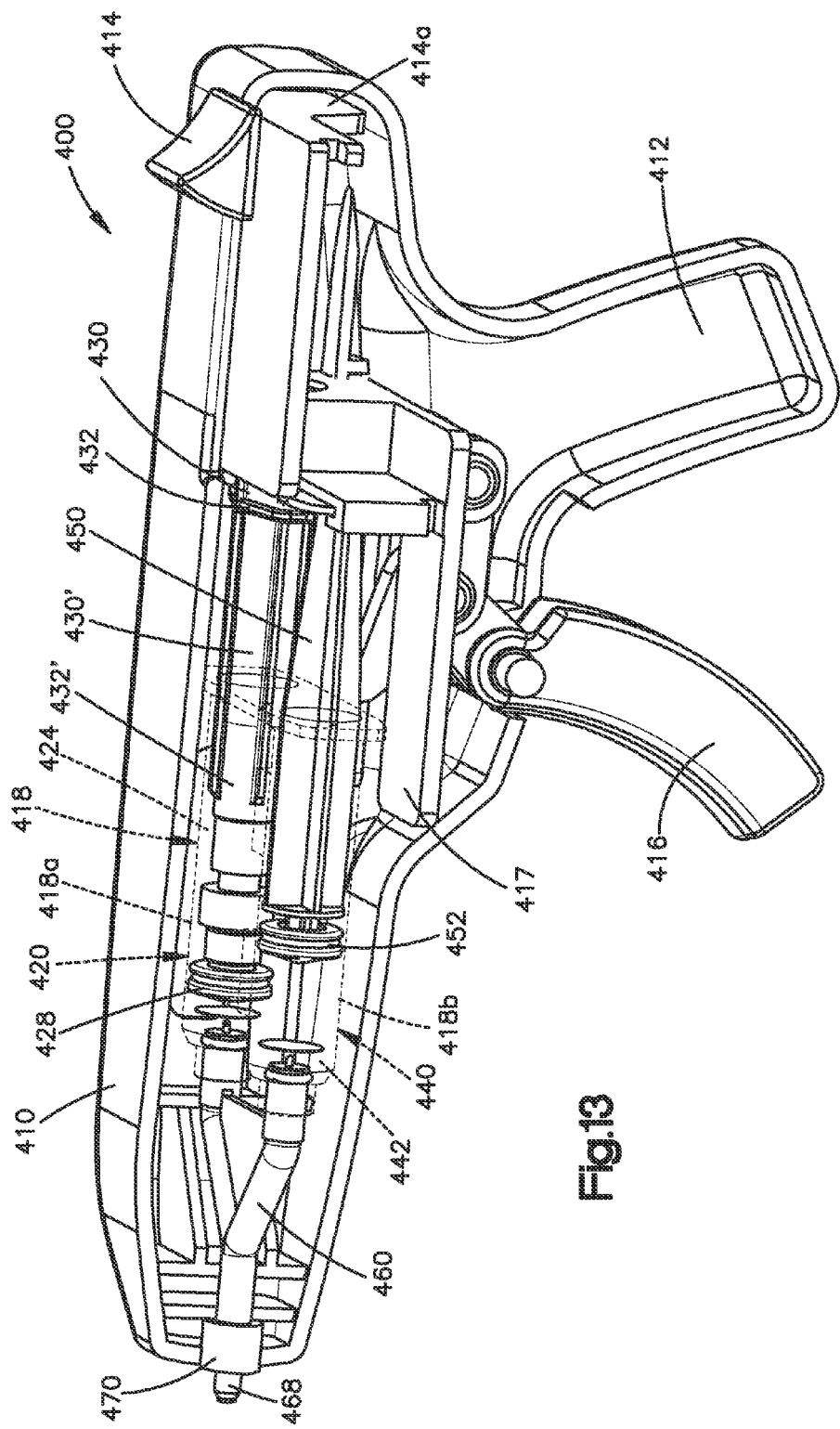
FIG. 13 is a cut-away perspective view of a sealant application apparatus constructed in accordance with another alternative embodiment.
Figure 14:
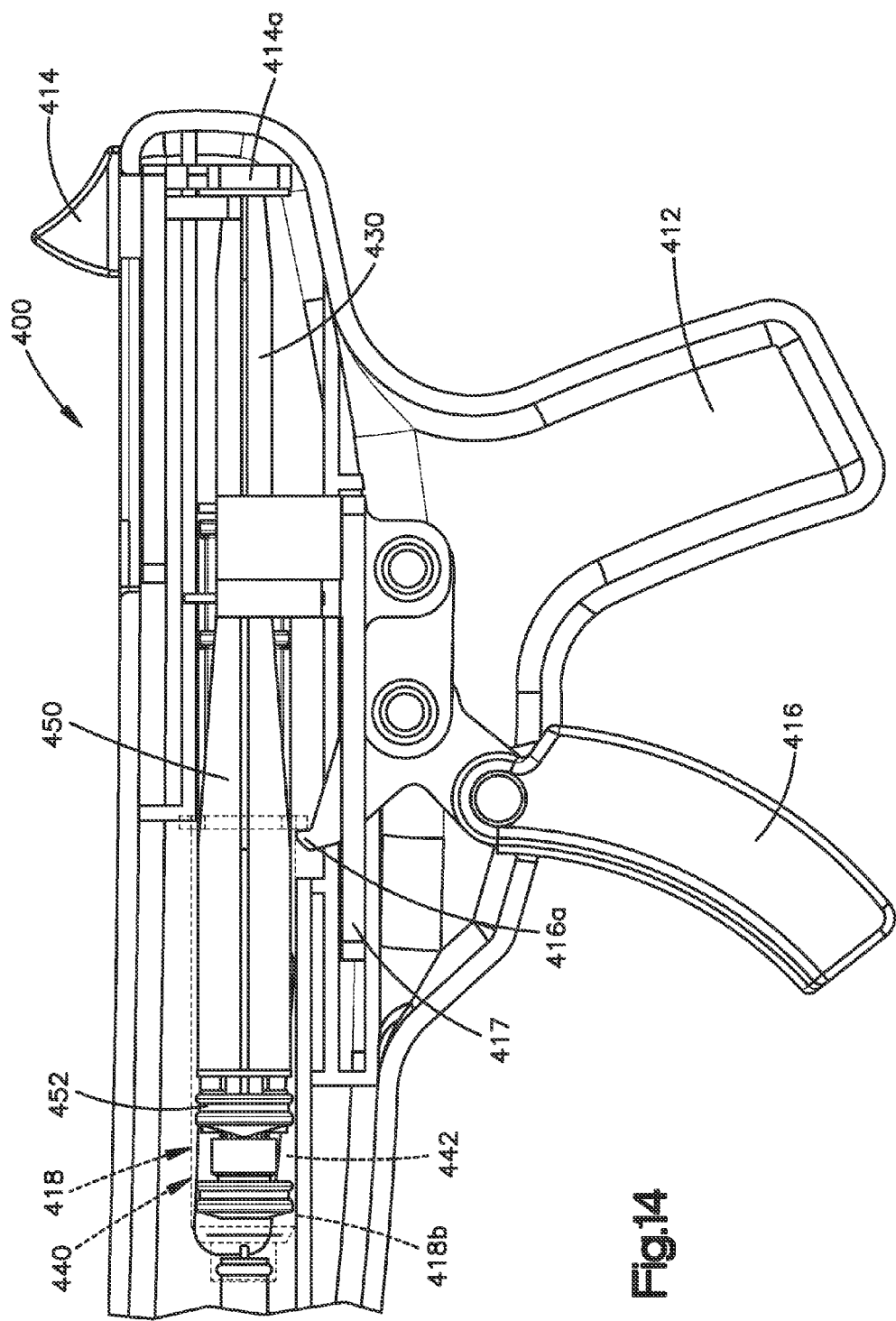
FIG. 14 is a cut-away side elevation view of the sealant application apparatus of FIG. 13.
Figure 15:
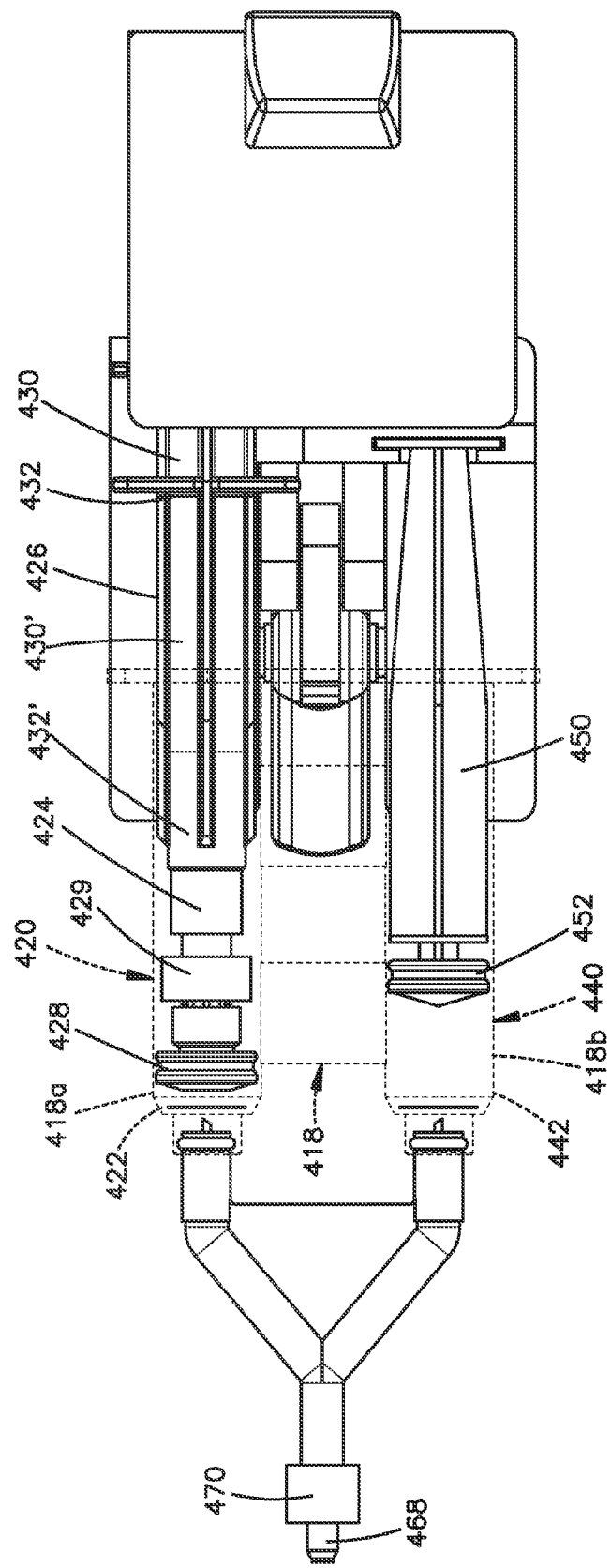
FIG. 15 is a top plan view of internal components of the sealant application apparatus of FIG. 13.
Figure 16:
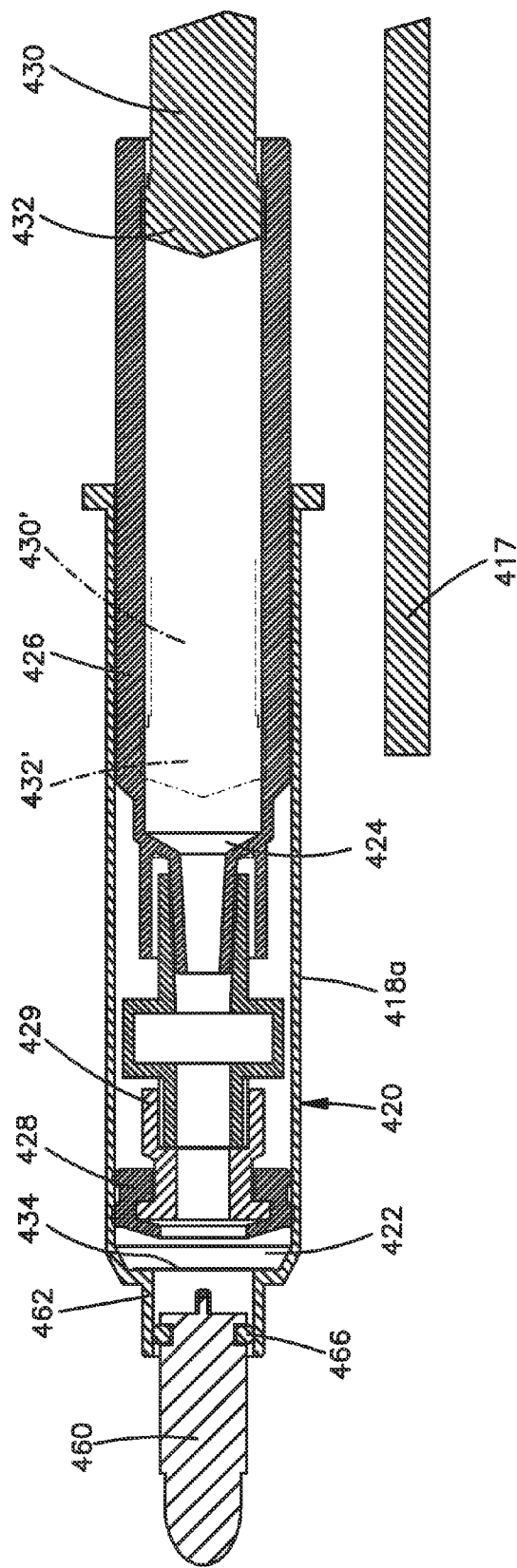
FIG. 16 is a sectional side elevation view of internal components of the sealant application apparatus of FIG. 13.
Figure 17:
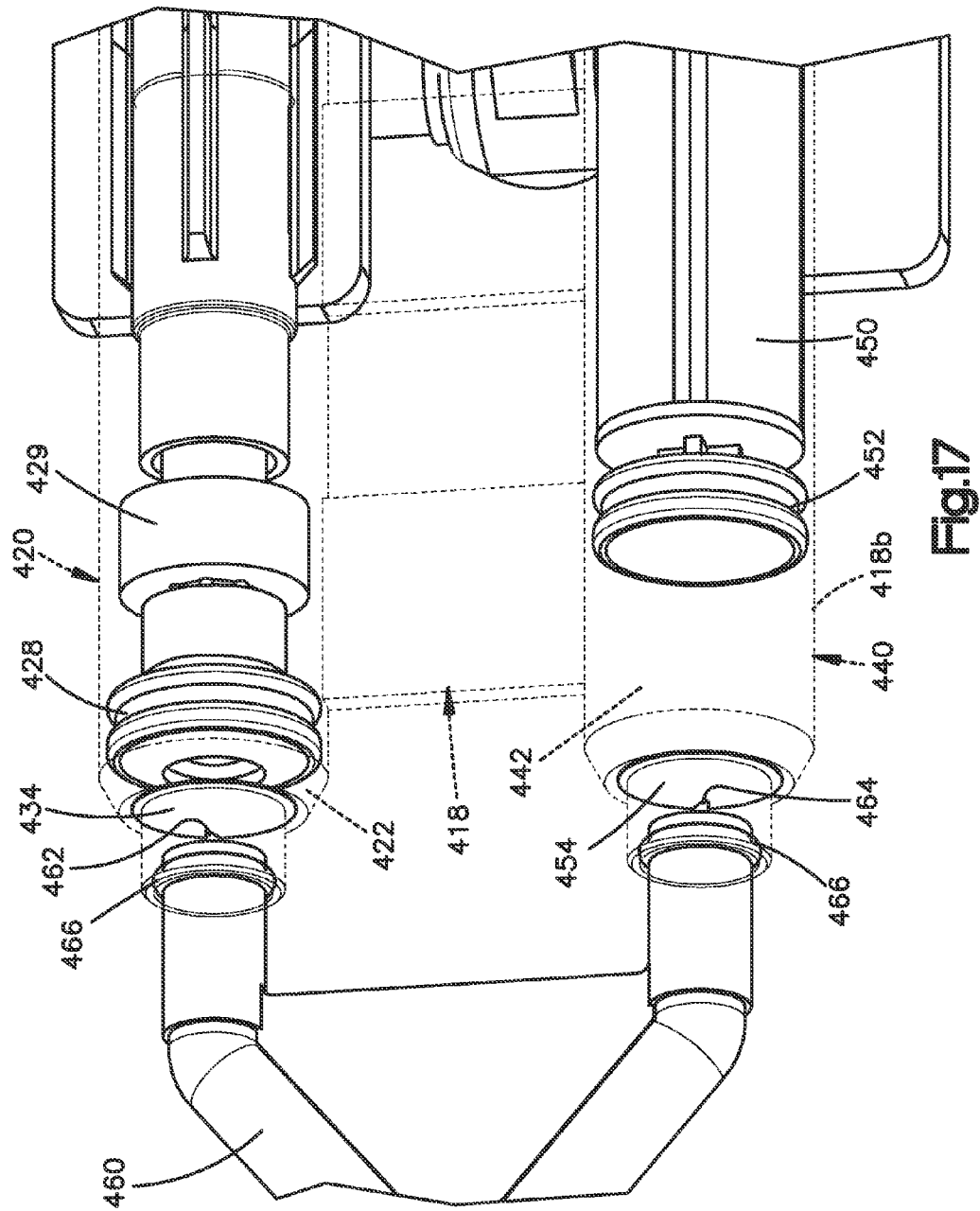
FIG. 17 is a perspective view of internal components of the sealant application apparatus of FIG. 13.
Figure 18:
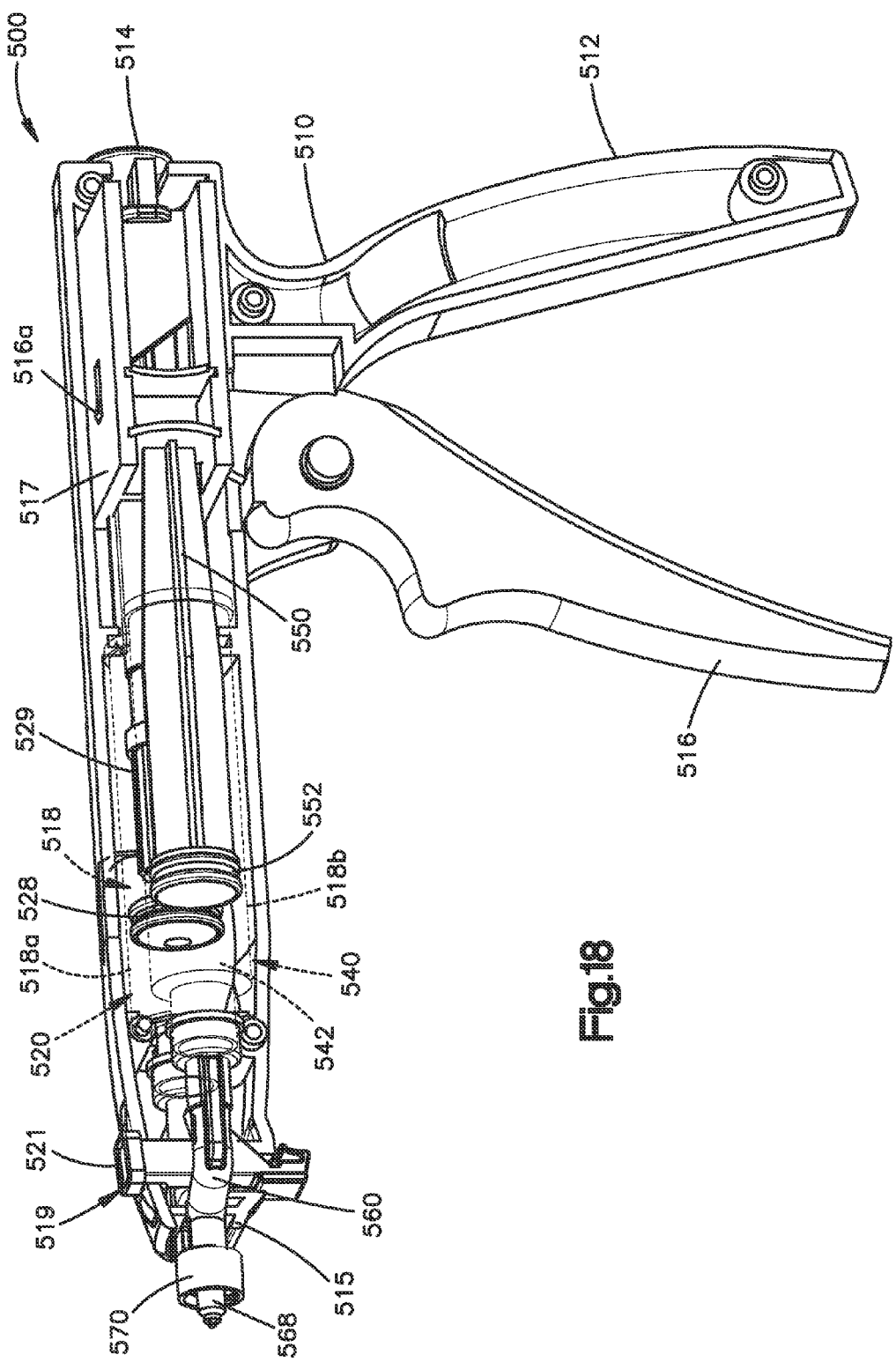
FIG. 18 is a cut-away perspective view of a sealant application apparatus constructed in accordance with another alternative embodiment.
Figure 19:
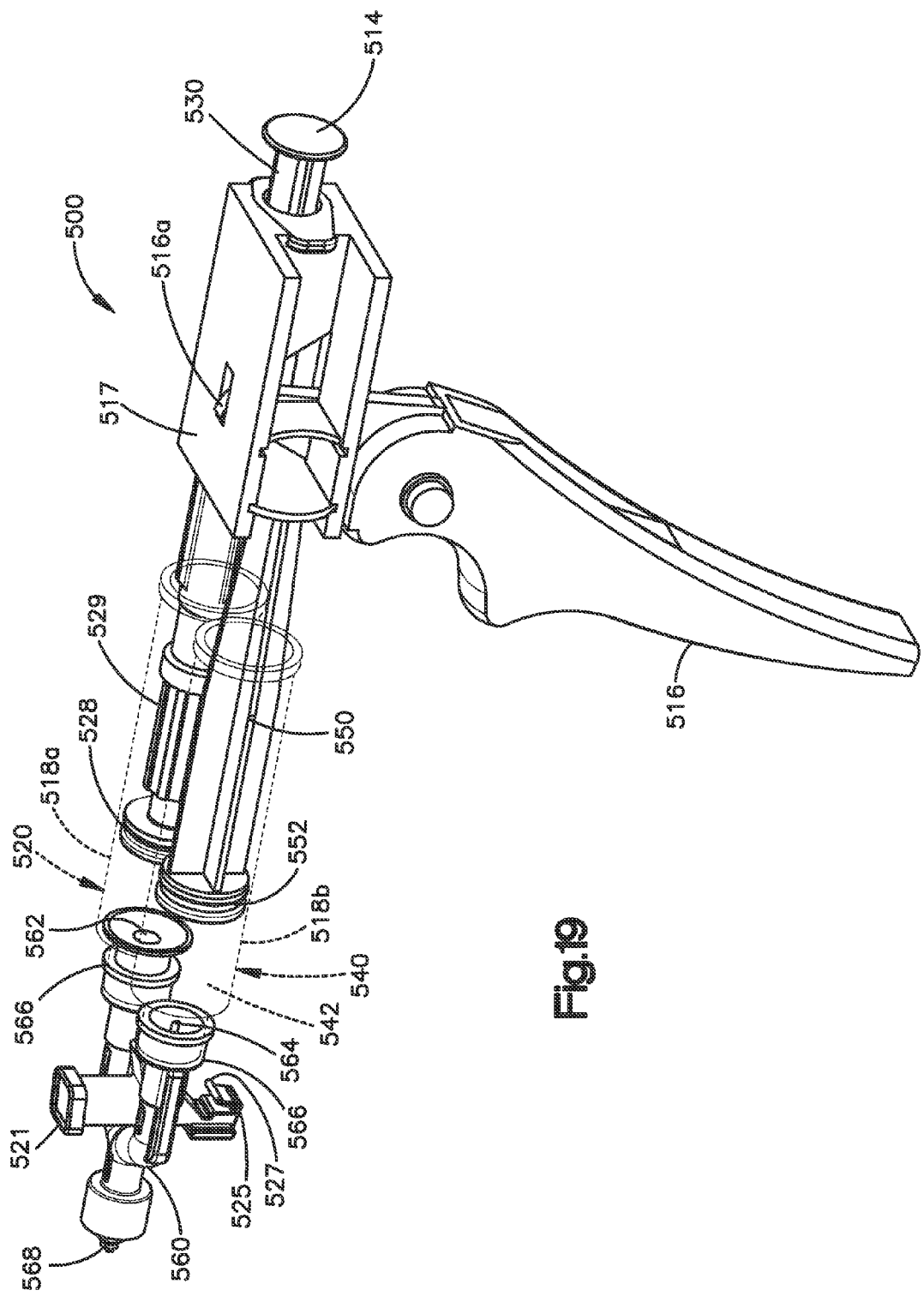
FIG. 19 is a cut-away perspective view of the sealant application apparatus of FIG. 18.
Figure 20:
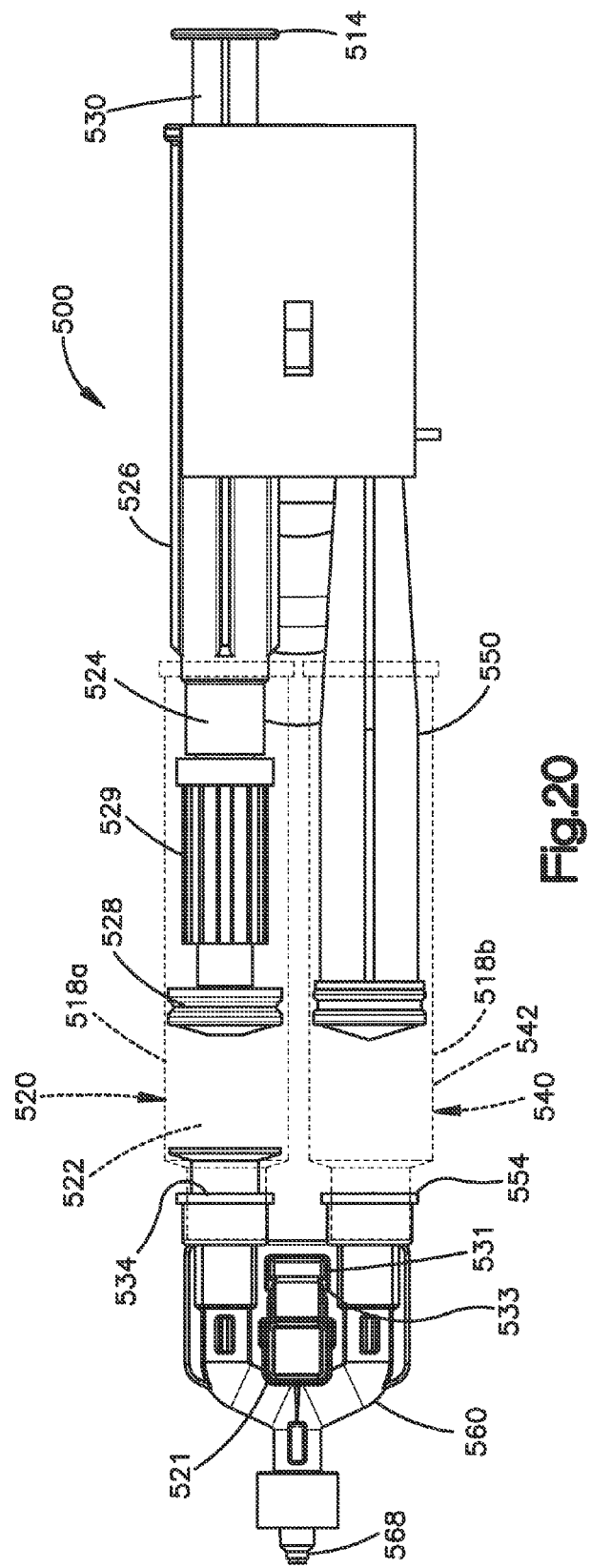
FIG. 20 is a top plan view of internal components of the sealant application apparatus of FIG. 18.
Figure 21:
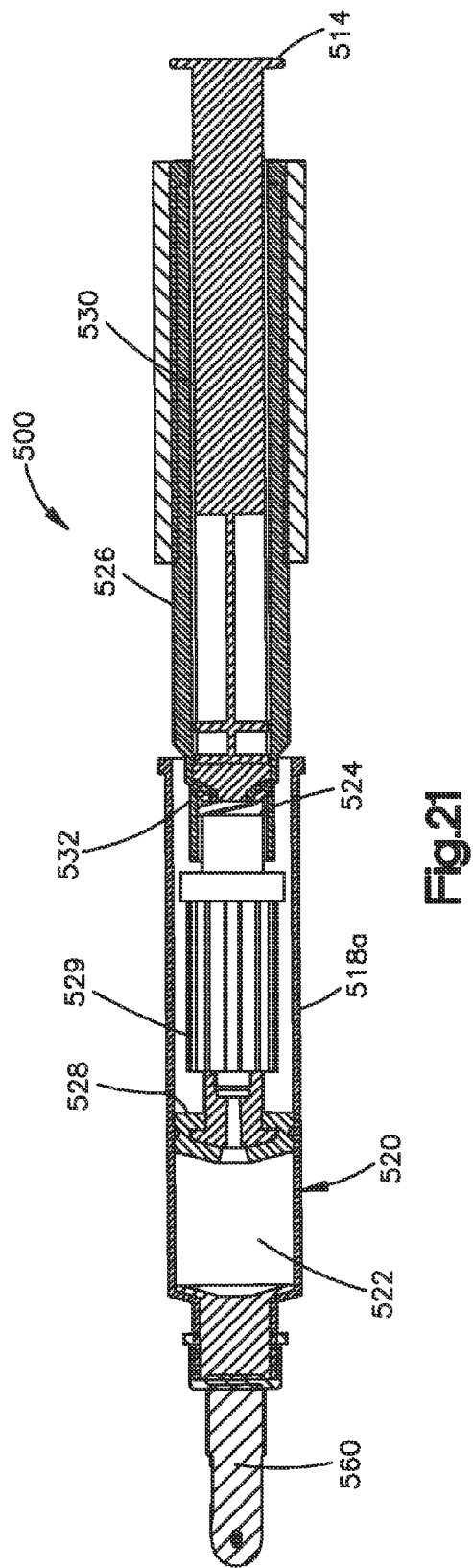
FIG. 21 is a sectional side elevation view of internal components of the sealant application apparatus of FIG. 18.
Figure 22:
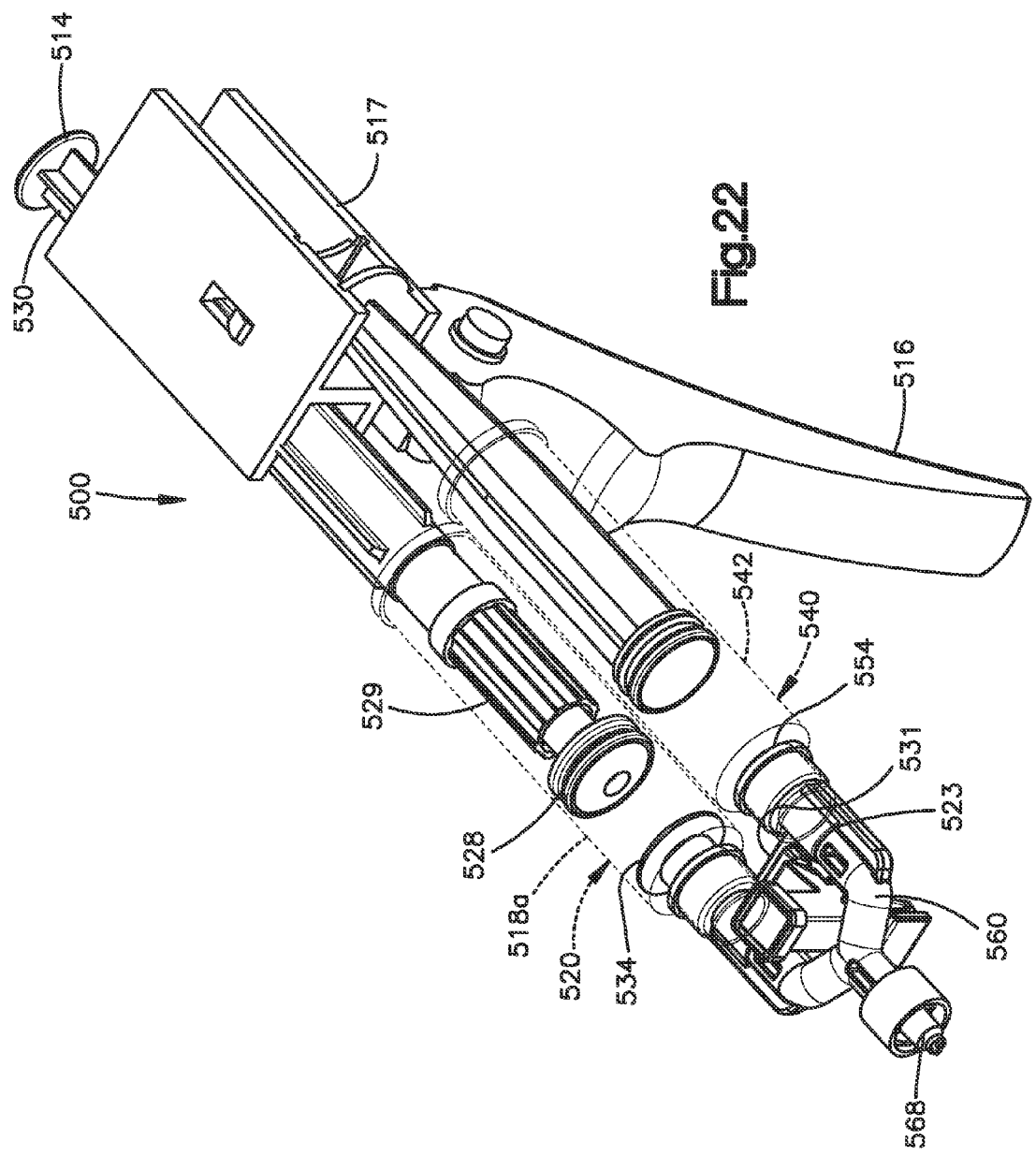
FIG. 22 is a perspective view of internal components of the sealant application apparatus of FIG. 18.

Referring to FIGS. 11 and 12, in some examples, a Y adapter 360 fluidly couples the first and second syringes 320, 340 with a nozzle to expel the contents from the apparatus 300. The Y adapter 360, in some examples, is engaged distally from the first and second valves 334, 354. The Y adapter 360, in an example, is Y-shaped and includes a single distal end and two branches at a proximal end with one of the branches sealingly engaged to a passageway leading from the first valve 334 and the other of the branches sealingly engaged to a passageway leading from the second valve 354.

In some examples, the nozzle is disposed at the distal end of the Y adapter 360. Fluid passageways can extend from the proximal end of the Y adapter 360, through each of the branches of the Y adapter 360, to the nozzle. The nozzle, in an example, is a dual nozzle, such that the passageways running from each of the first and second syringes 320, 340 do not converge into a single passageway before or proximal to the nozzle. In a further example, a mixing chamber 372 is attached to the distal end of the Y adapter 360, the mixing chamber 372 being configured to allow the contents of the first and second syringes 320, 340 to comingle and mix to form a sealant mixture, for instance. The distal end of the Y adapter 360 can include a collar 370 or other engagement device for attachment of the mixing chamber 372. In an example, the collar 370 is a luer lock collar for engagement of a mixing chamber 372 having a mating luer connection. In another example, the passageways can converge prior to the distal end of the Y-adapter to enable the components to mix prior to leaving the Y adapter, thereby eliminating the need for a separate mixing chamber 372, as described above.

The mixing chamber 372 can include a nozzle to expel the sealant mixture (for example, the tissue sealant) for application to a desired surface (for instance, the dural tissue). In an example, the nozzle is an atomizing nozzle to atomize the sealant mixture during use of the apparatus 300 and facilitate application of the sealant mixture (for example, the tissue sealant) for application to the desired surface (for instance, the dural tissue).

In a further example, the apparatus 300 can include a fourth syringe selectively fluidly coupled through the second valve 354 to the second syringe 340 in a manner similar to the first syringe 320 and the third syringe sleeve 326. In one example, the fourth syringe is empty and does not include any substance to mix with the second substance in the second syringe 340. In another example, the fourth syringe can include, or can be configured to receive or include, a substance for mixing with the second substance within the second syringe 340. In either example, the presence of the fourth syringe allows mixing of the first and third substances (and, optionally, the second and fourth substances) using the trigger 316 rather than the first actuator 314. That is, the first and second valves 334, 354 can be set to allow fluid communication between the first syringe 320 and the third syringe sleeve 326 and between the second syringe 340 and the fourth syringe. The trigger 316 can then be actuated back and forth to move the first and second plungers 330, 350 back and forth within the first and second syringes 320, 340 to move the first substance back and forth between the first syringe 320 and the third syringe sleeve 326 and to move the second substance back and forth between the second syringe 340 and the fourth syringe. In this way, the first actuator 314 can be eliminated from the apparatus 300, thereby further simplifying operation of the apparatus 300.

Referring to the example apparatus 300 shown in FIGS. 8-12 and described above, in use, the user positions the first valve lever 334A to position the first valve 334 to allow fluid communication between the first syringe 320 and the third syringe sleeve 326. The user can then hold the apparatus 300 by the handle 312 using one hand and push the first actuator 314 forward (distally with respect to the apparatus 300). Movement of the first actuator 314 causes distal movement of the first plunger 330 with respect to the first syringe sleeve 321. This motion of the first plunger 330 forces the first substance out of the first syringe 320 and into the third syringe sleeve 326, allowing the first and third substances (for instance, the reconstitution fluid and the lyophilized PEG) of the first and third chambers 322, 324 to mix. The first actuator 314 can then be moved back and forth to move the further mix and agitate the first and third substances. In an example, the housing 310 can include a window to allow the user to view the mixture of the first and third substances to determine whether sufficient mixing of the first and third substances has occurred. The spring 329 of the third syringe sleeve 326 distally biases the third plunger 328 to force the first and third substances out of the third chamber 324 and into the first syringe 320 as the first and third substances mix. As briefly described above, a fourth syringe can be included with the apparatus 300 in order to mix the second substance with another substance and/or to allow mixing of the substances using the trigger 316 rather than the first actuator 314. In an example, the fourth syringe can be spring biased like the third syringe sleeve 326 described above.

Once the first and third substances are sufficiently mixed, the user can disengage the interlock mechanism to allow the trigger 316 to be pulled and/or reposition the first and second valves 334, 354 to allow fluid communication from the first and second syringes 320, 340 to the Y adapter 360. Subsequent actuation of the trigger 316 causes the carriage 317 to push the first and second plungers 330, 350 distally with respect to the first and second syringe sleeves 321, 341 to force the contents of the first and second syringes 320, 340 (for instance, the reconstituted PEG from the first syringe 320 and the periodate and water mixture from the second syringe 340) out of the first and second syringes 320, 340, through the passageways and first and second valves 334, 354, and into the passageways of the Y adapter 360. The contents of the first and second syringes 320, 340 exit the Y adapter 360 through the dual nozzle and enter the mixing chamber 372 to mix together and form the sealant mixture. The sealant mixture is then expelled from the apparatus 300 through the atomizing nozzle of the mixing chamber 372 for application to the desired surface (for instance, the dural tissue incision).

Referring now to FIGS. 13-17, in another example, a sealant application apparatus 400 is shown for housing an amount of components for a sealant (a tissue sealant, for instance), which, in some examples, during use of the apparatus 400, are mixed together and expelled from the apparatus 400 at a desired location (a dural tissue incision, for instance) to aid in sealing the location to protect against leakage (CSF leakage from the incision, for instance). In some examples, some aspects of the apparatus 400 are substantially similar to aspects of the apparatus 100 described above. As such, some structures, features, and components of the apparatus 400 are shown in FIGS. 13-17 with numbering similar to substantially similar structures, features, and components of the apparatus 100, as shown in FIGS. 1-5, and function in manners substantially similar to those described above with respect to the apparatus 100. Accordingly, the description of such substantially similar features is omitted below and, instead, is incorporated from the corresponding descriptions above with respect to the apparatus 100.

In the example shown in FIGS. 13-17, the apparatus 400 includes a valve 429 within a first syringe sleeve 418A to selectively separate first and second chambers 422, 424 and the contents thereof. In an example, the valve 429 is a one-way check valve 429. The check valve 429, in an example, is engaged with a distal end of an inner syringe sleeve 426 telescopically disposed within the first syringe sleeve 418A. In an example, a third plunger tip 428 is engaged to a distal end of the check valve 429.

In an example, a first plunger 430 is coupled to a first actuator 414, which is accessible by the user to enable the user to move the first plunger 430. In an example, a portion of the first actuator 414 extends outwardly from a housing 410 to allow the user to grip and move the first actuator 414. In an example, the first actuator 414 is slidable with respect to the housing 410. The first actuator 414, in some examples, includes a portion 414A which abuts a proximal end of the first syringe plunger 430, such that forward motion of the first actuator 414 causes the first plunger 430 to move distally within the inner syringe sleeve 426 to force a second substance out of the inner syringe sleeve 426, through the check valve 429, and into the first chamber 422 to comingle with a first substance. Because, in certain examples, the valve 429 is a one-way check valve 429, the first actuator 414 cannot be used to move the first and second substances back and forth for mixing and agitation. Because of this, once the first and second substances are comingled in the first chamber 422, the apparatus 400 can be shaken to mix and agitate the first and second substances. In an example, the first actuator 414 is configured to lock into a carriage 417 once the first actuator 414 is pushed forward to force the second substance out of the inner syringe sleeve 426, through the check valve 429, and into the first chamber 422 to comingle with the first substance.

Referring to the example apparatus 400 shown in FIGS. 13-17 and described above, in use, the user holds the apparatus 400 by a handle 412 using one hand and pushes the first actuator 414 forward (distally with respect to the apparatus 400). Movement of the first actuator 414 causes distal movement of the first plunger 430 and a first plunger tip 432 with respect to the inner syringe sleeve 426 to a distal position within the inner syringe sleeve 426 (the first plunger 430 and a first plunger tip 432 in the distal position denoted as 430' and 432' in FIGS. 13, 15, and 16). This motion of the first plunger 430 forces the second substance through the check valve 429 and into the first chamber 422, allowing the first and second substances (for instance, the lyophilized PEG and the reconstitution fluid) of the first and second chambers 422, 424 to mix. The apparatus 400 can then be shaken for a period of time sufficient to agitate and mix the first and second substances within the first chamber 422. In an example, the housing 410 can include a window to allow the user to view the mixture of the first and second substances to determine whether sufficient mixing of the first and second substances has occurred. Once the first and second substances are sufficiently mixed, the user disengages an interlock mechanism to allow a trigger 416 to be pulled. Initial pulling of the trigger 416 disengages a hook 416A from a dual syringe sleeve 418 and starts motion of the carriage 417 within the housing 410 to push on the first plunger 430 and a second plunger 450. Movement of the trigger 416 and carriage 417 initially moves the dual syringe sleeve 418 distally with respect to the housing 410 to cause first and second puncture members 462, 464 to come into contact with and pierce first and second puncture seals 434, 454 at the distal ends of the first syringe sleeve 418A and a second syringe sleeve 418B. After the first and second puncture seals 434, 454 are pierced, further actuation of the trigger 416 causes the carriage 417 to push the first and second plungers 430, 450 distally with respect to the first and second syringe sleeves 418A, 418B to force the contents of the first and second syringes 420, 440 (for instance, a reconstituted PEG from the first syringe 420 and a periodate and water mixture from the second syringe 440) out of the first and second syringes 420, 440 and into passageways of a Y adapter 460. In an example, because the first plunger tip 432 is positioned within the inner syringe sleeve 426 in the distal position 432', movement of the first plunger 430 also moves the first plunger tip 432, the check valve 429 with the third plunger tip 428, and the inner syringe sleeve 426 in unison within the first syringe sleeve 418A to force the contents of the first syringe 420 into the Y adapter 460. In this way, the first plunger 430, the first plunger tip 432, the check valve 429 with the third plunger tip 428, and the inner syringe sleeve 426 essentially act together as a syringe plunger within the first syringe sleeve 418A. The contents of the first and second syringes 420, 440 exit the Y adapter 460 through the dual nozzle 468 and optionally enter a mixing chamber to mix together and form the sealant mixture. The sealant mixture is then expelled from the apparatus 400 through an atomizing nozzle of the mixing chamber for application to the desired surface (for instance, the dural tissue incision).

Referring now to FIGS. 18-22, in another example, a sealant application apparatus 500 is shown for housing an amount of components for a sealant (a tissue sealant, for instance), which, in some examples, during use of the apparatus 500, are mixed together and expelled from the apparatus 500 at a desired location (a dural tissue incision, for instance) to aid in sealing the location to protect against leakage (CSF leakage from the incision, for instance). In some examples, some aspects of the apparatus 500 are substantially similar to aspects of the apparatus 100 described above. As such, some structures, features, and components of the apparatus 500 are shown in FIGS. 18-22 with numbering similar to substantially similar structures, features, and components of the apparatus 100, as shown in FIGS. 1-5, and function in manners substantially similar to those described above with respect to the apparatus 100. Accordingly, the description of such substantially similar features is omitted below and, instead, is incorporated from the corresponding descriptions above with respect to the apparatus 100.

In the example shown in FIGS. 18-22, the apparatus 500 includes a housing 510 surrounding internal components of the apparatus 100. The apparatus 500 includes a valve 529 within a first syringe sleeve 518a to selectively separate first and second chambers 522, 524 and the contents thereof. In an example, the valve 529 is a one-way check valve 529. The check valve 529, in an example, is engaged with a distal end of an inner syringe sleeve 526 telescopically disposed within the first syringe sleeve 518a. In an example, a third plunger tip 528 is engaged to a distal end of the check valve 529.

In an example, a first plunger 530 is coupled to a first actuator illustrated as a plunger head 514 that can be integrally or discretely connected to the plunger 530. The first actuator 514, is accessible by the user to enable the user to move the first plunger 530. In an example, a portion of the first actuator 514 extends rearwardly out from the housing 510 to allow the user to grip and move the first actuator 514. In an example, the first actuator 514 is slidable with respect to the housing 510, such that forward motion of the first actuator 514 relative to the housing 510 causes the first plunger 530 to move distally within the inner syringe sleeve 526 to force a second substance out of the inner syringe sleeve 526, through the check valve 529, and into the first chamber 522 to comingle with a first substance. Because, in certain examples, the valve 529 is a one-way check valve 529, the first actuator 514 cannot be used to move the first and second substances back and forth for mixing and agitation. Because of this, once the first and second substances are comingled in the first chamber 522, the apparatus 500 can be shaken to mix and agitate the first and second substances. In an example, the first actuator 514 is configured to lock into a carriage 517 once the first actuator 514 is pushed forward to force the second substance out of the inner syringe sleeve 526, through the check valve 529, and into the first chamber 522 to comingle with the first substance.

Referring to the example apparatus 500 shown in FIGS. 18-22 and described above, in use, the user holds the apparatus 500 by a handle 512 using one hand and pushes the first actuator 514 forward (distally with respect to the apparatus 500). Movement of the first actuator 514 causes distal movement of the first plunger 530 and a first plunger tip 532 with respect to the inner syringe sleeve 526 to a distal position within the inner syringe sleeve 526. This motion of the first plunger 530 forces the second substance through the check valve 529 and into the first chamber 522, allowing the first and second substances (for instance, the lyophilized PEG and the reconstitution fluid) of the first and second chambers 522, 524 to mix. The apparatus 500 can then be shaken for a period of time sufficient to agitate and mix the first and second substances within the first chamber 522.

In an example, the housing 510 can include a window to allow the user to view the mixture of the first and second substances to determine whether sufficient mixing of the first and second substances has occurred. Once the first and second substances are sufficiently mixed, the user engages an actuator 519 move a Y adapter 560 relative to the housing 510. The housing 510 includes at least one support rib, such as a plurality of support ribs 515, that support the Y adapter 560 such that the Y adapter 560 is translatable relative to the housing 510.

As described above with respect to the apparatus 400, the actuator 519 could be in the form of a trigger, or as illustrated with respect to the apparatus 500, the actuator 519 can be in the form of a button 521 that extends from a location outside the housing 510 to a location inside the housing 510. The button 521 includes a beveled cam surface 523 and a flexible tab 525 having an engagement member in the form of a catch 527 disposed at the distal end of the tab 525. The Y adapter 560 includes a plate 531 having a forward edge 533 that abuts the beveled cam surface 523. Accordingly, when the button 521 is depressed, the cam surface 523 translates downward against the forward edge 533, thereby causing the plate 531 and the rest of the Y adapter 560 to translate proximally relative to the housing 510 so as to cause first and second puncture members 562, 564 to come into contact with and pierce first and second puncture seals 534, 554 at the distal ends of the first syringe sleeve 518a and a second syringe sleeve 518b. The flexible tab 525 flexes against the housing 510 until the puncture members 562, 564 pierce the puncture seals 534, 554, at which point the catch engages the housing 510 so as to prevent the button 521 from inadvertently reversing upwards.

After the first and second puncture seals 534, 554 are pierced, the user disengages an interlock mechanism to allow a trigger 516 to be pulled. Initial pulling of the trigger 516 disengages a hook 516A from a dual syringe sleeve 518 and causes the carriage 517 to push the first and second plungers 530, 550 distally with respect to the first and second syringe sleeves 518a, 518b to force the contents of the first and second syringes 520, 540 (for instance, a reconstituted PEG from the first syringe 520 and a periodate and water mixture from the second syringe 540) out of the first and second syringes 520, 540 and into passageways of the Y adapter 560. In an example, because the first plunger tip 532 is positioned within the inner syringe sleeve 526 in the distal position, movement of the first plunger 530 also moves the first plunger tip 532, the check valve 529 with the third plunger tip 528, and the inner syringe sleeve 526 in unison within the first syringe sleeve 518a to force the contents of the first syringe 520 into the Y adapter 560. In this way, the first plunger 530, the first plunger tip 532, the check valve 529 with the third plunger tip 528, and the inner syringe sleeve 526 essentially act together as a syringe plunger within the first syringe sleeve 518a. The contents of the first and second syringes 520, 540 exit the Y adapter 560 through the dual nozzle 568 and optionally enter a mixing chamber to mix together and form the sealant mixture. The sealant mixture is then expelled from the apparatus 500 through an atomizing nozzle of the mixing chamber for application to the desired surface (for instance, the dural tissue incision).

In other examples, a method of using a self-contained sealant application apparatus, such as the apparatuses 100, 200, 300, 400, 500 described above, is contemplated. With reference to FIGS. 1-22 and to the description above, in some examples, the method includes actuating a first actuator to allow a first substance of a first chamber to comingle with a second substance of a second chamber. The first and second substances can then be mixed to form a first mixture. In further examples, a second actuator is actuated to urge the first mixture and a third substance of a third chamber together to mix to form a sealant mixture. The second actuator can be further actuated to urge the sealant mixture out of the application apparatus for application of the sealant mixture. In an example, mixing the first and second substances includes repeatedly actuating the first actuator to mix the first and second substances. In another example, mixing the first and second substances includes shaking the apparatus to mix the first and second substances. In an example, the second actuator is actuated to urge the first mixture and the third substance into a mixing chamber to mix and form the sealant mixture within the mixing chamber.

It should be appreciated throughout this disclosure that the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

It will be appreciated by those skilled in the art that changes could be made to the embodiments described above without departing from the broad inventive concept thereof. It is understood, therefore, that this invention is not limited to the particular embodiment disclosed, but it is intended to cover modifications within the spirit and scope of the present invention, for instance as defined by the appended claims.

What is claimed is:

1. A sealant application apparatus comprising:
   a first chamber including a first substance;
   a second chamber including a second substance, wherein the second chamber is in selective fluid communication with the first chamber;
   a third chamber including a third substance;
   a first actuator configured to cause fluid communication of the first and second chambers to allow the first and second substances to comingle and form a first mixture; and
   a second actuator configured to urge the first mixture and the third substance out of the sealant application apparatus.

2. The sealant application apparatus of claim 1, comprising a mixing chamber configured to receive and mix the first mixture and the third substance into sealant mixture prior to being urged out of the sealant application apparatus.

3. The sealant application apparatus of claim 1, comprising an atomizing nozzle configured to spray the first mixture and the third substance out of the sealant application apparatus.

4. The sealant application apparatus of claim 1, comprising a burst disc fluidly separating the first and second chambers, wherein actuation of the first actuator causes the burst disc to rupture to allow fluid communication of the first and second chambers.

5. The sealant application apparatus of claim 1, comprising a valve fluidly separating the first and second chambers, wherein actuation of the first actuator allows the first or second substance to pass therethrough to allow fluid communication of the first and second chambers.

6. The sealant application apparatus of claim 5, wherein the valve comprises a one-way check valve.

7. The sealant application apparatus of claim 6, wherein actuation of the first actuator urges the second substance through the one-way check valve and in to the first chamber to mix with the first substance.

8. The sealant application apparatus of claim 1, comprising a fourth chamber including a fourth substance, wherein the fourth chamber is in selective fluid communication with the third chamber.

9. The sealant application apparatus of claim 8, wherein the first actuator is configured to cause fluid communication of the third and fourth chambers to allow the third and fourth substances to comingle and form a second mixture.

10. The sealant application apparatus of claim 8, wherein a second actuator is configured to cause fluid communication of the third and fourth chambers to allow the third and fourth substances to comingle and form a second mixture.

11. The sealant application apparatus of claim 1, comprising a lock configured to fix the second actuator with respect to the sealant application apparatus to inhibit inadvertent urging of the first mixture and the third substance out of the sealant application apparatus.

12. The sealant application apparatus of claim 1, wherein the first, second, and third substances comprise tissue sealant components.

13. The sealant application apparatus of claim 1, wherein a first syringe includes the first and second chambers.

14. The sealant application apparatus of claim 1, wherein a first syringe includes the first chamber, and a second syringe includes the second chamber.

15. The sealant application apparatus of claim 1, wherein a third syringe includes the third chamber.

16. The sealant application apparatus of claim 1, wherein the second chamber includes a spring-actuated plunger configured to urge the first mixture out of the second chamber and into the first chamber.

17. A method of using a self-contained sealant application apparatus, the method comprising:
    actuating a first actuator to allow a first substance of a first chamber to comingle with a second substance of a second chamber;
    mixing the first and second substances to form a first mixture; and
    urging the first mixture and a third substance of a third chamber together to mix to form a sealant mixture; and
    urging the sealant mixture out of the application apparatus for application of the sealant mixture.

18. The method of claim 17, wherein mixing the first and second substances includes repeatedly actuating the first actuator to mix the first and second substances.

19. The method of claim 17, wherein mixing the first and second substances includes shaking the sealant application apparatus to mix the first and second substances.

20. The method of claim 17, wherein actuating the second actuator to urge the first mixture and the third substance together includes actuating the second actuator to urge the first mixture and the third substance into a mixing chamber to mix and form the sealant mixture.

21. The method of claim 17, wherein the urging steps are performed by actuating a second actuator.

22. The method of claim 17, wherein the urging steps are performed by actuating second and third actuators, respectively.

23. A sealant application apparatus comprising:
    a first chamber configured to receive a first substance;
    a second chamber configured to receive a second substance, wherein the second chamber is in selective fluid communication with the first chamber;
    a third chamber configured to receive a third substance;
    a first actuator configured to cause fluid communication of the first and second chambers to allow the first and second substances to comingle and form a first mixture; and
    a second actuator configured to urge the first mixture and the third substance out of the sealant application apparatus.

24. The sealant application apparatus of claim 23, comprising a mixing chamber configured to receive and mix the first mixture and the third substance into sealant mixture prior to being urged out of the sealant application apparatus.

25. The sealant application apparatus of claim 23, comprising an atomizing nozzle configured to spray the first mixture and the third substance out of the sealant application apparatus.

26. The sealant application apparatus of claim 23, comprising a burst disc fluidly separating the first and second chambers, wherein actuation of the first actuator causes the burst disc to rupture to allow fluid communication of the first and second chambers.

27. The sealant application apparatus of claim 23, comprising a valve fluidly separating the first and second chambers, wherein actuation of the first actuator allows the first or second substance to pass therethrough to allow fluid communication of the first and second chambers.

28. The sealant application apparatus of claim 27, wherein the valve comprises a one-way check valve.

29. The sealant application apparatus of claim 23, comprising a fourth chamber configured to receive a fourth substance, wherein the fourth chamber is in selective fluid communication with the third chamber.

30. The sealant application apparatus of claim 23, comprising a lock configured to fix the second actuator with respect to the sealant application apparatus to inhibit inadvertent urging of the first mixture and the third substance out of the sealant application apparatus.

31. The sealant application apparatus of claim 23, wherein a first syringe includes the first and second chambers.

32. The sealant application apparatus of claim 23, wherein a first syringe includes the first chamber, and a second syringe includes the second chamber.

33. The sealant application apparatus of claim 23, wherein a third syringe includes the third chamber.

34. The sealant application apparatus of claim 23, wherein the second chamber includes a spring-actuated plunger configured to urge the first mixture out of the second chamber and into the first chamber.

35. A sealant application apparatus comprising:
    a first chamber configured to retain a first substance;
    a second chamber configured to retain a second substance, wherein the second chamber is in selective fluid communication with the first chamber;
    a third chamber configured to retain a third substance;
    a first actuator configured to cause fluid communication of the first and second chambers to allow the first and second substances to comingle and form a first mixture; and
    a second actuator configured to urge the first mixture and the third substance out of the sealant application apparatus.

* * * * *